(12) United States Patent
Zhang et al.

(10) Patent No.: US 10,639,379 B2
(45) Date of Patent: *May 5, 2020

(54) HIGH AFFINITY CXCR4 SELECTIVE BINDING CONJUGATE AND METHOD FOR USING THE SAME

(71) Applicant: Mainline Biosciences LLC, Malvern, PA (US)

(72) Inventors: Junge Zhang, Malvern, PA (US); Liang Zeng Yan, Carmel, IN (US)

(73) Assignee: Mainline Biosciences LLC, Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/898,434

(22) Filed: Feb. 17, 2018

(65) Prior Publication Data

US 2019/0255185 A1  Aug. 22, 2019

Related U.S. Application Data

(60) Provisional application No. 62/554,354, filed on Sep. 5, 2017.

(51) Int. Cl.

| | | |
|---|---|---|
| A61K 38/10 | (2006.01) | |
| A61K 38/12 | (2006.01) | |
| C07K 5/00 | (2006.01) | |
| C07K 7/00 | (2006.01) | |
| C07K 16/00 | (2006.01) | |
| C07K 17/00 | (2006.01) | |
| A61K 38/00 | (2006.01) | |
| A61K 47/64 | (2017.01) | |
| A61K 38/16 | (2006.01) | |
| C07K 14/705 | (2006.01) | |
| C07K 14/71 | (2006.01) | |
| A61P 35/00 | (2006.01) | |
| C07K 19/00 | (2006.01) | |
| G01N 33/566 | (2006.01) | |
| A61P 31/18 | (2006.01) | |
| C07K 14/52 | (2006.01) | |
| A61K 47/00 | (2006.01) | |
| C07K 7/08 | (2006.01) | |

(52) U.S. Cl.
CPC .......... *A61K 47/642* (2017.08); *A61K 38/16* (2013.01); *A61K 47/00* (2013.01); *A61K 47/6425* (2017.08); *A61P 31/18* (2018.01); *A61P 35/00* (2018.01); *C07K 14/521* (2013.01); *C07K 14/70596* (2013.01); *C07K 14/71* (2013.01); *C07K 19/00* (2013.01); *G01N 33/566* (2013.01); *C07K 7/08* (2013.01)

(58) Field of Classification Search
None
See application file for complete search history.

(56) References Cited

U.S. PATENT DOCUMENTS

| | | | |
|---|---|---|---|
| 10,351,601 B2 * | 7/2019 | Zhang | ............... C07K 7/64 |
| 2011/0027175 A1 * | 2/2011 | Wester | ............ A61K 51/088 |
| | | | 424/1.69 |

FOREIGN PATENT DOCUMENTS

| | | | | |
|---|---|---|---|---|
| WO | WO-2012095527 A1 * | 7/2012 | ....... | C07K 14/43504 |
| WO | WO-2015185162 A1 * | 12/2015 | ............. | A61K 1/082 |

OTHER PUBLICATIONS

Costantini et al. "Peptides targeting chemokine receptor CXCR4: structural behavior and biological binding studies" J. Peptide Sci. 20:270-278. (Year: 2014).*

Li et al. "A designed peptide targeting CXCR4 displays anti-acute myelocytic leukemia activity in vitro and in vivo" Scientific Reports 4:6610 (Year: 2014).*

Oishi and Fujii "Peptide and peptidomimetic ligands for CXC chemokine receptor 4 (CXCR4)" Organic & Biomolecular Chemistry 10 :5720-5731 (Year: 2012).*

(Continued)

*Primary Examiner* — James H Alstrum-Acevedo
*Assistant Examiner* — Zachary J Miknis
(74) *Attorney, Agent, or Firm* — Don D. Cha; HDC IP Law, LLP

(57) ABSTRACT

The present invention provides a compound that can be used for targeted drug delivery, imaging a patient, or diagnosing a subject for a clinical condition which is believed to be associated with overexpression and/or upregulation of CXCR4. In particular, the present invention provides a high affinity CXCR4 selective binding ligand peptide conjugate (PC) of the Formula: P-(L-A)$_n$ (I) or a pharmaceutically acceptable salt thereof, and a method for using and producing the same. The high affinity CXCR4 selective binding ligand peptide conjugate (PC) of the invention is useful in diagnosing, treating or imaging a patient. In compound of Formula (I), n is an integer from 1 to the sum of (the total number of amino acid resides in P and the total number of side-chain functional group in the amino acid residue of P); each A is independently a diagnostic agent, a therapeutic agent, or an imaging agent; L is a linker or absent; and P is a high affinity CXCR4 selective binding peptidyl ligand. In particular, the invention provides to a targeted drug delivery or imaging a patient or diagnosing a patient for a disease of which overexpression and/or upregulation of CXCR4 is implicated, such as cancers, HIV infection, and immune disorders. Compositions and kits peptide conjugate of Formula I as well as methods for using and producing peptide conjugate of Formula I are disclosed herein.

20 Claims, No Drawings

Specification includes a Sequence Listing.

(56) References Cited

OTHER PUBLICATIONS

Tietz et al. "Design, synthesis and in vitro characterization of fluorescent and paramagnetic CXCR4-targeted imaging agents" Am. J. Nucl. Med. Mol. Imaging 3:372-383. (Year: 2013).*
Anonymous "T22 peptide—Potent CXCR4 antagonist" https://www.smart-bioscience.com/peptide-service/peptide-catalog/antimicrobial-peptides-amp/t22-peptide-cxcr4-antagonist/ (Year: 2016).*

* cited by examiner

HIGH AFFINITY CXCR4 SELECTIVE BINDING CONJUGATE AND METHOD FOR USING THE SAME

CROSS-REFERENCE TO RELATED APPLICATIONS

This application claims the priority benefit of U.S. Provisional Application No. 62/554,354, filed Sep. 5, 2017, which is incorporated herein by reference in its entirety.

FIELD OF THE INVENTION

The present invention relates to a high affinity CXCR4 selective binding ligand peptide conjugate ("PC") of the Formula: P-(L-A)$_n$ (I) or a pharmaceutically acceptable salt thereof, and a method for using and producing the same. In particular, the high affinity CXCR4 selective binding ligand peptide conjugate of the invention are useful in diagnosing, treating or imaging a patient. In compound of Formula (I), each A is independently a diagnostic agent, a therapeutic agent, or an imaging agent; L is a linker or absent; and P is a high affinity CXCR4 selective binding peptidyl ligand. In particular, the invention relates to a targeted drug delivery or imaging a patient or diagnosing a patient for a disease of which overexpression and/or upregulation of CXCR4 is implicated, such as cancers, HIV infection, and immune disorders. Compositions, kits and methods are disclosed herein for such uses.

BACKGROUND OF THE INVENTION

Studies have shown CXCL12 (also called stromal cell-derived factor-1 or SDF-1) and CXCR4, a chemokine and chemokine receptor pair play important roles in hematopoiesis, multiple stages of tumorigenesis, and embryonic development (Broxmeyer, H. E. et al., *Int. J. Hematol.* 2001, 74, 9-17; Horuk, R., *Nat. Rev. Drug Discov.* 2009, 8, 23-33). For example, activation of CXCR4 by CXCL12 has shown to direct leukocyte chemotaxis in the immune system in response to inflammation and progenitor cell migration during embryologic development. Activation of CXCR4 by CXCL12 has also been shown to mediate signaling pathway that is involved in breast cancer metastasis and memory T cell migration (Orimo, A., et al., *Cell* 2005, 121, 335-348). CXCR4, a G-protein-coupled receptor also known as fusin or CD184 (cluster of differentiation 184), is constitutively- or over-expressed in a wide variety of human cancers, promoting local tumor cell proliferation, survival and angiogenesis (Huang, E. H., et al., *J. Surg. Res.* 2009, 155, 231-236). It has also been reported that CXCR4 is a co-receptor for HIV entry and infection of host cells and has been evaluated as a potential HIV therapy (Tamamura, H., et al., *Biochem. Biophys. Res. Commun.* 1998, 253, 877-882; Oberlin, E. et al., *Nature*, 1996, 382, 833-835).

Reports have confirmed that CXCR4 is overexpressed in numerous human cancers. CXCR4 antagonism has been shown to disrupt tumor-stromal interactions, sensitize cancer cells to cytotoxic drugs, and reduce tumor growth and metastatic burden. Hence, CXCR4 is a target not only for potential therapeutic intervention of cancer treatment, but also for noninvasive monitoring of disease progression, therapeutic guidance, and other diagnostic purposes (Chatterjee, S. et al., *Adv Cancer Res.* 2014; 124:31-82). Binding and Interacting with CXCR4 have been suggested as a potential way of targeted drug delivery (Wang, Y. et al., *Curr Pharmcol Rep* (2016) 2:1-10).

Thus, it is believed that compounds having a moiety that can selectively bind CXCR4 (i.e., CXCR4 selective binding conjugate) can have a wide variety uses including, but not limited to, in treating a wide array of clinical conditions associated with activation or over-expression of CXCR4, diagnosing a patient, and in mediacl imaging.

Accordingly, there is a need for conjugates that can selectively bind to CXCR4.

SUMMARY OF THE INVENTION

One aspect of the invention provides a high affinity CXCR4 selective binding ligand peptide conjugate ("PC"). In some embodiments, the high affinity CXCR4 selective binding ligand peptide conjugate comprises a peptidyl moiety that has a high affinity for selectively binding to CXCR4 which is linked or attached to (optionally via a linker) to an active component. The active component can be a diagnostic agent, a therapeutic agent, or an imaging agent. In this manner, the peptidyl moiety selectively binds to CXCR4 receptor and delivers the active component.

In one particular embodiment, the high affinity CXCR4 selective binding ligand peptide conjugate is a compound of the Formula:

$$P\text{-}(L\text{-}A)_n \qquad\qquad I$$

or a pharmaceutically acceptable salt thereof, where n is an integer from 1 to the total number of amino acid residue within P that have a side-chain functional group; P is a high affinity CXCR4 selective binding peptide moiety; each L is independently an optional linker (i.e., it can be absent or be a linker such as polyethylene glycol moiety or other linkers known to one skilled in the art); and each A is independently an active component such as a diagnostic agent, a therapeutic agent, or an imaging agent. While it is readily apparent to those skilled in the art, it should be noted that when L is absent, A is attached directly to P, e.g., through a chemical bond, such as an amide bond or an ester bond. In one particular embodiments, compound of Formula I is used in diagnosis of or treatment of a clinical condition associated with overexpression or upregulation of CXCR4, i.e., A is a diagnostic agent or a drug. Typically, compound of Formula I includes (i) a peptidyl ligand (i.e., a peptide moiety) that has a high affinity to CXCR4, (2) optionally a linker, and (3) an active component, e.g., a diagnostic agent, a therapeutic agent (e.g., a drug), or an imaging agent (e.g., a radioactive moiety, a fluorescent moiety, etc.).

In one particular embodiment, moiety P (i.e., a high affinity CXCR4 selective binding peptide moiety) is of the Formula:

(SEQ ID NO: 1)

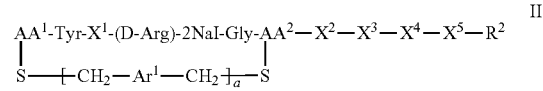

wherein
a is 0 or 1;
AA$^1$ along with the sulfur atom that is attached thereto is 3-mercaptopropionic acid, optionally substituted cysteine, or optionally substituted homocysteine;
AA$^2$ along with the sulfur atom that is attached thereto is cysteine or homocysteine;
Ar$^1$ is an optionally substituted aryl;

$X^1$ is Arg, Dap, Dab, Orn, Lys, Dap(iPr), Dab(iPr), Orn(iPr), or Lys(iPr);

$X^2$ is Arg, Dap, Dab, Orn, Lys, Dap(iPr), Dab(iPr), Orn(iPr), Lys(iPr), D-Arg, D-Dap, D-Dab, D-Orn, D-Lys, D-Dap(iPr), D-Dab(iPr), D-Orn(iPr), D-Lys(iPr), or absent;

$X^3$ is Lys, Gly or absent;

$X^4$ is Lys, Phe, 2Nal, 1Nal, the D-isomer thereof, Gly, or absent;

$X^5$ is Lys, Gly or absent; and $R^2$ is —$OR^4$ or —$NHR^5$, wherein $R^4$ and $R^5$ are H, alkyl, optionally substituted aryl or optionally substituted aralkyl.

It should be appreciated that the optional linker and moiety A (i.e., -L-A moiety) of Formula I can be attached to any of the amino acids via a functional group that is present in the side-chain thereof.

Yet in other embodiments, compounds of the invention are of the Formula:

(SEQ ID NO: 2)

III

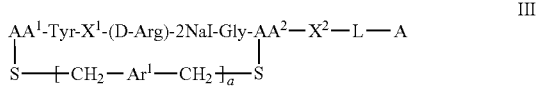

or a pharmaceutically acceptable salt thereof, wherein a is 0 or 1;

$AA^1$ along with the sulfur atom that is attached thereto is 3-mercaptopropionic acid, optionally substituted cysteine, or optionally substituted homocysteine;

$AA^2$ along with the sulfur atom that is attached thereto is cysteine or homocysteine;

$Ar^1$ is an optionally substituted aryl;

$X^1$ is Arg, Dap, Dab, Orn, Lys, Dap(iPr), Dab(iPr), Orn(iPr), or Lys(iPr);

$X^2$ is Arg, Dap, Dab, Orn, Lys, Dap(iPr), Dab(iPr), Orn(iPr), Lys(iPr), D-Arg, D-Dap, D-Dab, D-Orn, D-Lys, D-Dap(iPr), D-Dab(iPr), D-Orn(iPr), D-Lys(iPr), or absent;

L and A are as defined herein.

Another aspect of the invention provides a diagnostic kit comprising a high affinity CXCR4 selective binding ligand peptide conjugate disclosed herein, e.g., a compound of Formula I where A is a diagnostic agent.

Yet another aspect of the invention provides a composition comprising (i) a high affinity CXCR4 selective binding ligand peptide conjugate disclosed herein and (ii) a pharmaceutically acceptable carrier, diluent, excipient or a combination thereof.

Still another aspect of the invention provides a method for imaging cancer cells in a patient. Such a method generally includes administering to a patient an imaging effective amount of a high affinity CXCR4 selective binding ligand peptide conjugate of the invention, e.g., compound of Formula I where A is an imaging agent; and imaging cancer cells in said patient using an imaging apparatus.

Yet other aspects of the invention provide a method for treating cancer in a patient by administering a therapeutically effective amount of a pharmaceutical composition that includes a compound of Formula I, where A is a therapeutic agent for cancer (i.e., a cancer or oncology drug).

It should be appreciated that when A of compound of Formula I is a diagnostic agent or an imaging agent, compounds of the invention can be used in a diagnostic or an imaging kit, respectively.

In one specific embodiments of the invention, compound of Formula I is used in treating a patient suffering from rheumatoid arthritis, pulmonary fibrosis, HIV infection, or a cancer. The method includes administering a therapeutically effective amount of a compound of Formula I (where A is a therapeutic agent for treating rheumatoid arthritis, pulmonary fibrosis, HIV infection, or a cancer, respectively) to a patient in need of such a treatment. Typical cancer that is treated with a compound of Formula I includes, but are not limited to, breast cancer, pancreatic cancer, melanoma, prostate cancer, kidney cancer, neuroblastoma, non-Hodgkin's lymphoma, lung cancer, ovarian cancer, colorectal cancer, multiple myeloma, glioblastoma multiforme, and chronic lymphocytic leukemia.

Another aspect of the invention provides a method for targeted drug delivery for a clinical condition associated with overexpression and/or upregulation of CXCR4. Exemplary clinical conditions include, but are not limited to, rheumatoid arthritis, pulmonary fibrosis, HIV infection, and cancer. Specific examples of cancers include breast cancer, pancreatic cancer, melanoma, prostate cancer, kidney cancer, neuroblastoma, non-Hodgkin's lymphoma, lung cancer, ovarian cancer, colorectal cancer, multiple myeloma, glioblastoma multiforme, and chronic lymphocytic leukemia.

Another aspect of the invention provides a method for disease diagnosis and monitoring for a clinical condition associated with overexpression and/or upregulation of CXCR4. Exemplary clinical conditions include, but are not limited to, rheumatoid arthritis, pulmonary fibrosis, HIV infection, and cancer. Specific examples of cancers include breast cancer, pancreatic cancer, melanoma, prostate cancer, kidney cancer, neuroblastoma, non-Hodgkin's lymphoma, lung cancer, ovarian cancer, colorectal cancer, multiple myeloma, glioblastoma multiforme, and chronic lymphocytic leukemia.

Another aspect of the invention provides a kit for disease diagnosis and monitoring for a clinical condition associated with overexpression and/or upregulation of CXCR4. Exemplary clinical conditions include, but are not limited to, rheumatoid arthritis, pulmonary fibrosis, HIV infection, and cancer. Specific examples of cancers include breast cancer, pancreatic cancer, melanoma, prostate cancer, kidney cancer, neuroblastoma, non-Hodgkin's lymphoma, lung cancer, ovarian cancer, colorectal cancer, multiple myeloma, glioblastoma multiforme, and chronic lymphocytic leukemia.

DETAILED DESCRIPTION OF THE INVENTION

CXCR4 plays an important role in immune and inflammatory responses in various diseases and disorders, including cancer, viral infections, as well as autoimmune pathologies such as rheumatoid arthritis. The present invention is based at least in part on reducing or preventing overexpression or activation of CXCR4 to treat, diagnose or image a clinical condition associated with CXCR4 overexpression and/or activation. As used herein, the term "overexpression and/or activation" refers to expression of a gene above its normal (i.e., control) or baseline level and/or activation of CXCR4 above its normal, control or baseline level, respectively.

The terms "normal," "baseline level" and "control level" are used interchangeably herein and refer to expression and/or activity level of CXCR4 in subject(s) that do not have a disease or a clinical condition associated with overexpression and/or activation of CXCR4, such as those disclosed herein. In some embodiments, the baseline level can be a normal level, meaning the level in a sample from a normal subject that do not have a clinical condition associated with overexpression and/or activation (or activity) of CXCR4. This allows a determination based on the baseline level of CXCR4 expression or its biological activity, i.e., whether a sample to be tested or evaluated for disease or a clinical condition has a measureable increase, decrease, or substantially no change in CXCR4 expression or activation as compared to the baseline level.

It should be appreciated that the overexpression and/or activation of CXCR4 can also be determined by comparing the sample result with a positive control. The term "positive control" as used herein refers to a level of CXCR4 expression and/or activation (or activity) established in a sample from a subject or from a population of individuals, where the sample was believed, based on data from that sample, to have a disease or a clinical condition associated with overexpression and/or activation of CXCR4 (e.g., cancer, autoimmune disease such as rheumatoid arthritis and viral infection, such as HIV infection).

In other embodiments, the baseline level can be established from a previous sample from the subject being tested, so that the disease progression or regression of the subject can be monitored over time and/or the efficacy of treatment can be evaluated.

Some aspects of the invention provide compounds that have a high affinity toward CXCR4 that is attached to a diagnostic agent, a therapeutic agent or an imaging agent, optionally through a linker. Such compounds include a CXCR4 binding moiety and an active component. The invention also provides methods for using the same, e.g., in targeted delivery of therapeutics to treat clinical conditions manifested by or associated with overexpression and/or activation of CXCR4. As used herein, the term "high affinity" means the compound or the moiety that binds to CXCR4 has a binding constant ($K_b$) of about 10 nM or less, typically about 3 nM or less, and often 1 nM or less. Alternatively, the term "high affinity" means the compound or the moiety that binds to CXCR4 has 50% binding inhibition concentration ($IC_{50}$) of about 30 nM or less, typically about 10 nM or less and often about 3 nM or less. Methods for determining binding constant and $IC_{50}$ are well known to one skilled in the art. See, for example, commonly assigned U.S. provisional patent application No. 62/384,132, filed Sep. 6, 2016, and 62/505,064, filed May 11, 2017, and commonly assigned PCT patent application no. PCT/US17/50106, filed Sep. 5, 2017, all of which are incorporated herein by reference in their entirety. In particular, the values $K_b$ and $IC_{50}$ are determined using the CXCR4/$^{125}$I-SDF-1α binding assay described in the above referenced provisional patent applications. The term "about" when referring to a numeric value means±20%, typically ±10% and often ±5% of the numeric value.

In one particular aspect of the invention, a high affinity CXCR4 selective binding ligand peptide conjugate ("PC") is of the Formula:

$$P\text{-}(L\text{-}A)_n \qquad\qquad\qquad I$$

or a pharmaceutically acceptable salt thereof, wherein
n is an integer from 1 to the sum of (the total number of amino acids in P and the total number of side-chain functional group), typically n is 1 to the number of amino acids in P, or n is 1 to the number of amino acids in P that have a side-chain with a functional group, often n is an integer of 1 to 5, more often n is an integer from 1 to 3;

A is one or more diagnostic agents, a therapeutic agents, or imaging agents;
each L is independently a bifunctional linker or absent; When L is absent, A is attached to P, e.g., through a chemical bond, such as an amide bond or an ester bond; and
P is a high affinity CXCR4 selective binding peptidyl ligand (i.e., a peptide moiety that selectively binds to CXCR4).

The variable n is an integer from 1 to the sum of (the total number of amino acids in P and the total number of side-chain functional group). Typically, n is an integer from 1 to 7, often from 1 to 5, more often from 1 to 3 and most often 1 or 2. For example, when there are a total of 7 amino acid residues in P and has two lysine groups (which have a side-chain functional group —$NH_2$), then n can be an integer from 1 to 9 (7 amino acid residue of P+2 side-chain functional groups). In this manner, all of the functional groups of P can be attached to -L-A moiety.

The moiety A in compound of Formula I can be attached to any portion of the P moiety. Typically, A moiety is attached to the N-terminal end or the C-terminal end of said peptide (the P moiety), or to a function group that is present on the side-chain of the amino acid residue of said peptide, or a combination of any one of the positions thereof. In some embodiments, compound of Formula I has a plurality of A moieties.

In one particular embodiment, P is a high affinity CXCR4 binding peptidyl of the Formula:

SEQ ID NO: 1

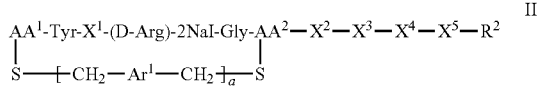

wherein:
a is 0 or 1;
$AA^1$ along with the sulfur atom that is attached thereto is 3-mercaptopropionic acid, optionally substituted cysteine, or optionally substituted homocysteine;
$AA^2$ along with the sulfur atom that is attached thereto is cysteine or homocysteine;
$Ar^1$ is an optionally substituted aryl;
$X^1$ is Arg, Dap, Dab, Orn, Lys, Dap(iPr), Dab(iPr), Orn(iPr), or Lys(iPr);
$X^2$ is Arg, Dap, Dab, Orn, Lys, Dap(iPr), Dab(iPr), Orn(iPr), Lys(iPr), D-Arg, D-Dap, D-Dab, D-Orn, D-Lys, D-Dap(iPr), D-Dab(iPr), D-Orn(iPr), D-Lys(iPr), or absent;
$X^3$ is Lys, Gly or absent;
$X^4$ is Lys, Phe, 2Nal, 1Nal, the D-isomer thereof, Gly, or absent;
$X^5$ is Lys, Gly or absent; and
$R^2$ is —$OR^4$ or —$NHR^5$, wherein $R^4$ and $R^5$ are H, alkyl, optionally substituted aryl, or optionally substituted aralkyl.

Moiety -L-A of Compound of Formula I can be attached to $AA^1$ (e.g., to α-amino group of cysteine or homocysteine) and/or $R^4$ and/or $R^5$, or $R^4$ and $R^5$ can be -L-A, where L is optionally a linker and A is a therapeutic agent, a diagnostic agent, or an imaging agent. Still further the moiety -L-A can be attached to the α-amino group of the N-terminal amino acid or a functional group of the side-chain of any of the amino acids of the peptidyl moiety.

Yet in other embodiments, A is an imaging agent. One particular example of a useful imaging agent of the invention includes a positron-emitting radioisotope such $^{34}$Cl, $^{45}$Ti, $^{51}$Mn, $^{61}$Cu, $^{63}$Zn, $^{68}$Ga, $^{11}$C, $^{13}$N, $^{15}$O, $^{18}$F. Typically, the positron-emitting radioisotope is attached to the linker or as a part of the linker (L moiety).

Another example of a useful imaging agent includes a radioactive metal isotope that is coordinated (i.e., chelated) to a chelating group. Particularly useful radioactive metal isotope include technetium, rhenium, gallium, gadolinium, indium, copper and a combination thereof. Appropriate chelating groups for a particular radioactive metal isotope are well known to one skilled in the art. For example, ferrocene and its derivatives, ethylenediaminetetraacetic acid ("EDTA"), its derivatives, a peptidyl moiety Dap-Asp-Cys and its derivatives (see U.S. Pat. No. 7,128,893), and others known in the art.

Yet another example of a useful imaging agent includes a contrasting agent. Contrasting agents are widely used, for example, in magnetic resonance imaging (MM). Wide variety of contrasting agents are known to one skilled in the art including gadobenate, gadobutrol, gadodiamide, gadofosveset, gadopentetate, gadoterate, gadoteridol, gadoversetamide, gadoxetate, and iron oxide.

Still another example of a useful imaging agent includes a fluorescent dye, such as fluorenylmethyloxycarbonyl (FMOC) and its derivatives, an AlexaFluor dye, an Oregon Green dye, a fluoresceins, a BODIPY (boron-dipyrromethene) dye, a cyanine dye, a rhodamine dye, a DyLight dye, and Texas Red.

In other embodiments, A is a diagnostic agent. Exemplary diagnostic agents that can be used in compound of the invention include an imaging agent, an isotopic agent, or a radioactive agent.

Yet in other embodiments, linker L comprises a functional group that is capable of releasing A in vivo. In this manner, the moiety A is released in vivo. Suitable functional groups that is capable of releasing A depends on the nature of the function group on moiety A that is linked to the linker. For example, when the function group on A is a hydroxyl group (i.e., —OH) or an amino group (—NH$_2$), the functional group on L can be a carboxylate such that an ester bond or an amide bond, respectively, is formed between A and L. If the functional group on A is a carboxylic acid, the corresponding functional group on L can be a hydroxyl group or an amino group to form an ester bond or an amide bond, respectively. Other suitable functional groups on L that is capable releasing A in vivo are well known to one skilled in the art including a disulfide bond linkage, an ester linkage, a thiol-maleimide linkage, and the like.

Still yet in other embodiments, A is a therapeutic agent. Suitable therapeutic agents include those that are known to one skilled in the art for treatment of cancer, autoimmune disease (e.g., rheumatoid arthritis), viral infection (e.g., HIV infection), etc. Exemplary therapeutic agents that are useful in compounds of the invention include, but are not limited to, bleomycin, daunorubicin, doxorubicin, docetaxel, irinotecan, monomethyl auristatin E, mertansine, paclitaxel, SN-38, tesirine, tubulysin, vinca alkaloids, and an analog or derivative thereof, HIV protease inhibitors, HIV fusion inhibitors, HIV reverse transcriptase inhibitors, HIV integrase inhibitors, HIV entry inhibitors, and therapeutics for autoimmune diseases.

Specific examples of high affinity CXCR4 selective binding ligand peptide conjugates of the invention include, but are not limited to:

cyclo[Phe-Tyr-Lys(iPr)-(D-Arg)-2Nal-Gly-(D-Glu)]-Lys(iPr)-(mini-PEG6)-Cys(S-paclitaxel)-Gly-NH$_2$, wherein the cyclic structure is formed between the α-amino of Phe connected to the side chain of D-Glu (SEQ ID NO:3); or R$^a$-cyclo[Cys-Tyr-Lys(iPr)-(D-Arg)-2Nal-Gly-Cys]-Lys(iPr)-R$^b$ (SEQ ID NO:4);

R$^a$-cyclo[hCys-Tyr-Lys(iPr)-(D-Arg)-2Nal-Gly-Cys]-Lys(iPr)-R$^b$ (SEQ ID NO:5);

R$^a$-cyclo[Cys-Tyr-Lys(iPr)-(D-Arg)-2Nal-Gly-hCys]-Lys(iPr)-R$^b$ (SEQ ID NO:6); and (SEQ ID NO: 7)

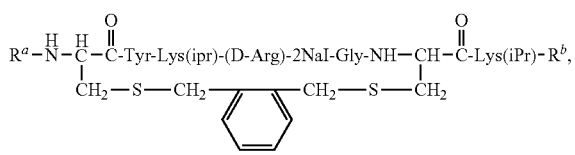

wherein

R$^a$ is acetyl-, acetyl-Cys(S-paclitaxel)-, or acetyl-Cys(S-paclitaxel)-(mini-PEG6)-; and R$^b$ is glycyl-amide, glycyl-Cys(S-paclitaxel)-amide, or (mini-PEG6)-Cys(S-paclitaxel)-amide, provided at least one of R$^a$ or R$^b$ comprises 5-paclitaxel.

In some embodiments, compounds of the invention are of the Formula:

(SEQ ID NO: 2)

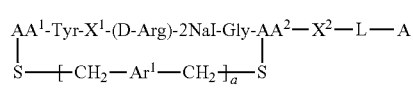

III or a pharmaceutically acceptable salt thereof, wherein:

a is 0 or 1;

AA$^1$ along with the sulfur atom that is attached thereto is 3-mercaptopropionic acid, optionally substituted cysteine, or optionally substituted homocysteine, wherein A is optionally attached to α-amino group of said cysteine or homocysteine;

AA$^2$ along with the sulfur atom that is attached thereto is cysteine or homocysteine;

Ar$^1$ is an optionally substituted aryl;

X$^1$ is Arg, Dap, Dab, Orn, Lys, Dap(iPr), Dab(iPr), Orn(iPr), or Lys(iPr);

X$^2$ is Arg, Dap, Dab, Orn, Lys, Dap(iPr), Dab(iPr), Orn(iPr), Lys(iPr), D-Arg, D-Dap, D-Dab, D-Orn, D-Lys, D-Dap(iPr), D-Dab(iPr), D-Orn(iPr), D-Lys(iPr), or absent;

L is optionally a linker; and

A is a therapeutic agent, a diagnostic agent or an imaging agent.

Within these embodiments, in some instances a is 0. Still in other instances, a is 1. Yet in other instances, AA$^1$ together with the sulfur atom that is attached thereto is 3-mercaptopropionic acid. Still yet in other instances, AA$^1$ together with the sulfur atom that is attached thereto is cysteine. In other instances, AA$^1$ together with the sulfur atom that is attached thereto is homocysteine.

Still in other embodiments, AA$^2$ together with the sulfur atom that is attached thereto is cysteine. In yet other embodiments, AA$^2$ together with the sulfur atom that is attached thereto is homocysteine.

Yet in other embodiments, A in compounds of Formula III is an imaging agent.

In other embodiments, A in compounds of Formula III is a therapeutic agent. Exemplary therapeutic agents within compounds of Formula III include, but are not limited to, bleomycin, calicheamicin, daunorubicin, docetaxel, doxorubicin, irinotecan, mertansine, monomethyl auristatin E, paclitaxel, SN-38, tesirine, topotecan, tubulysin, *vinca* alkaloids, and an analog or derivative thereof, and a combination thereof.

L can be any biocompatible bifunctional linker such as polyethylene glycol (PEG), e.g., in the form of $H_2N-CH_2CH_2-(PEG)m-CH_2CH_2-COOH$, $HOOC-CH_2CH_2-(PEG)m-CH_2CH_2-COOH$, or $H_2N-CH_2CH_2-(PEG)m-CH_2CH_2-NH_2$, natural and unnatural amino acids or a polyamino acid (PAA), where m is an integer from 0 to 100, typically 1 to 50, often 1 to 25, and more often 1 to 10. Generally, when L is a polymer (e.g., PEG, PAA), the total number of monomer within the chain is from about 1 (i.e., a monomer) to about 20, typically from about 1 to about 10, and often from about 1 to 6.

Still yet in other embodiments, A in compounds of Formula III is a diagnostic agent, such as a radioactive agent, fluorescent agent, etc. Such imaging agents are well known to one skilled in the art. For example, contrast agents for magnetic resonance imaging agents, ultrasound contrast agents, and radio contrast agents. See, for example, en.wikipedia.org/wiki/Contrast agent.

Still further, combinations of the various groups described herein can form other embodiments. In this manner, a variety of compounds are embodied within the present invention.

Another aspect of the invention provides a diagnostic kit comprising a high affinity CXCR4 selective binding ligand peptide conjugate described herein where A of compound of Formula I is a diagnostic agent.

Yet another aspect of the invention provides a composition comprising a compound of Formula I and a pharmaceutically acceptable carrier. Pharmaceutically acceptable carrier can include a diluent, an excipient, a flavoring agent, an adjuvant, a binder, a stabilizer, coloring agent, or a combination thereof. Generally, "pharmaceutically acceptable carrier" refers to any excipient that is useful in preparing a pharmaceutical composition that is generally safe, non-toxic and neither biologically nor otherwise undesirable, and includes excipient that is acceptable for veterinary use as well as human pharmaceutical use.

The present invention includes pharmaceutical compositions comprising at least one compound of the invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention are administered in a therapeutically effective amount by any of the accepted modes of administration for agents that serve similar utilities. Suitable dosage ranges are typically 1-500 mg daily, typically 1-100 mg daily, and often 1-30 mg daily, depending on numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases is typically able, without undue experimentation and in reliance upon personal knowledge and the disclosure of this application, to ascertain a therapeutically effective amount of the compounds of the invention.

Typically, compounds of the invention are administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. Typical manner of administration is generally oral using a convenient daily dosage regimen which can be adjusted according to the degree of affliction.

A compound or compounds of the invention, together with one or more conventional adjuvants, carriers, or diluents, can be placed into the form of pharmaceutical compositions and unit dosages. The pharmaceutical compositions and unit dosage forms can be comprised of conventional ingredients in conventional proportions, with or without additional active compounds or principles, and the unit dosage forms can contain any suitable effective amount of the active ingredient commensurate with the intended daily dosage range to be employed. The pharmaceutical compositions can be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention can be formulated in a wide variety of oral administration dosage forms. The pharmaceutical compositions and dosage forms can comprise a compound or compounds of the invention or pharmaceutically acceptable salts thereof as the active component. The pharmaceutically acceptable carriers can be either solid or liquid. Solid form preparations include powders, tablets, pills, capsules, cachets, suppositories, and dispersible granules. A solid carrier can be one or more substances which can also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges can be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions can be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and can contain, in addition to the active component, colorants, flavors, stabilizers, buffers, artificial and natural sweeteners, dispersants, thickeners, solubilizing agents, and the like.

The compounds of the invention can also be formulated for parenteral administration (e.g., by injection, for example bolus injection or continuous infusion) and can be presented in unit dose form in ampoules, pre-filled syringes, small volume infusion or in multidose containers with an added preservative. The compositions can take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and can contain formulatory agents such as preserving, wetting, emulsifying or suspending, stabilizing and/or dispersing agents. Alternatively, the active ingredient can be in powder form, obtained by aseptic isolation of sterile solid or by lyophilization from solution for constitution before use with a suitable vehicle, e.g., sterile, pyrogen-free water.

The compounds of the invention can be formulated for topical administration to the epidermis as ointments, creams or lotions, or as a transdermal patch. Ointments and creams can, for example, be formulated with an aqueous or oily base with the addition of suitable thickening and/or gelling agents. Lotions can be formulated with an aqueous or oily base and will in general also contain one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention can be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention can also be formulated for vaginal administration. Pessaries, tampons, creams, gels, pastes, foams or sprays containing in addition to the active ingredient such carriers as are known in the art to be appropriate.

The compounds of the invention can be formulated for nasal administration. The solutions or suspensions are applied directly to the nasal cavity by conventional means, for example, with a dropper, pipette or spray. The formulations can be provided in a single or multidose form. In the latter case of a dropper or pipette, this can be achieved by the patient administering an appropriate, predetermined volume of the solution or suspension. In the case of a spray, this can be achieved for example by means of a metering atomizing spray pump.

The compounds of the invention can be formulated for aerosol administration, particularly to the respiratory tract and including intranasal administration. The compound will generally have a small particle size for example of the order of five (5) microns or less. Such a particle size can be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol can conveniently also contain a surfactant such as lecithin. The dose of drug can be controlled by a metered valve. Alternatively the active ingredients can be provided in a form of a dry powder, for example, a powder mix of the compound in a suitable powder base such as lactose, starch, starch derivatives such as hydroxypropylmethyl cellulose and polyvinylpyrrolidine (PVP). The powder carrier typically forms a gel in the nasal cavity. The powder composition can be presented in unit dose form, for example, in capsules or cartridges of e.g., gelatine or blister packs from which the powder can be administered by means of an inhaler.

When desired, formulations can be prepared with enteric coatings adapted for sustained or controlled release administration of the active ingredient. For example, the compounds of the invention can be formulated in transdermal or subcutaneous drug delivery devices. These delivery systems are advantageous when sustained release of the compound is necessary or desired and when patient compliance with a treatment regimen is crucial. Compounds in transdermal delivery systems are frequently attached to a skin-adhesive solid support. The compound of interest can also be combined with a penetration enhancer, e.g., Azone (1-dodecylazacycloheptan-2-one). Sustained release delivery systems can be inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are typically in unit dosage forms. In such form, the preparation is often subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: *The Science and Practice of Pharmacy* 1995, edited by E. W. Martin, Mack Publishing Company, 19th edition, Easton, Pa.

When it is possible that, for use in therapy, therapeutically effective amounts of a compound of Formula I, as well as pharmaceutically acceptable salts thereof, can be administered as the raw chemical, it is possible to present the active ingredient as a pharmaceutical composition. Accordingly, the disclosure further provides pharmaceutical compositions, which include therapeutically effective mounts of compounds of Formula I or pharmaceutically acceptable salts thereof or a prodrug thereof, and one or more pharmaceutically acceptable carriers, diluents, or excipients. When applied to a combination, the term refers to combined amounts of the active ingredients that result in the therapeutic effect, whether administered in combination, serially, or simultaneously. The compounds of Formula I and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of Formula I, or a pharmaceutically acceptable salt thereof or a prodrug thereof, with one or more pharmaceutically acceptable carriers, diluents, or excipients.

When the compositions of this disclosure comprise a combination of a compound of the present disclosure and one or more additional therapeutic or prophylactic agent, both the compound and the additional agent are usually present at dosage levels of between about 10 to 150%, and more typically between about 10 and 80% of the dosage normally administered in a monotherapy regimen.

Still another aspect of the invention provides a method for imaging cancer cells in a patient comprising administering to a patient an imaging effective amount of a high affinity CXCR4 selective binding ligand peptide conjugate of Formula I, where A is an imaging agent, and imaging cancer cells in said patient using an imaging apparatus. The imaging apparatus used depends on the nature of imaging agent A of compound of Formula I. For example, if A is a positron-emitting radioisotope, then the imaging apparatus used is a PET scan, and when A is a contrasting agent, then the imaging apparatus can be a computed topography apparatus or an MII apparatus. When A is a radioactive isotope, the imaging apparatus can be an x-ray machine or other similar device.

One particular aspect of the invention provides a method for treating cancer in a patient. The method comprises administering a therapeutically effective amount of a compound of Formula I (where A is a cancer drug) or a pharmaceutical composition comprising a compound of Formula I (where A is a cancer drug) to a cancer patient.

Another particular aspect of the invention provides a diagnostic or an imaging kit comprising a high affinity CXCR4 selective binding ligand peptide conjugate (PC) of Formula I, where A is a diagnostic agent or an imaging agent, respectively.

Still another particular aspect of the invention provides a method for treating a patient suffering from rheumatoid arthritis, pulmonary fibrosis, HIV infection, or a cancer. The method includes administering a therapeutically effective amount of a compound of Formula I to a patient in need of treatment thereof. In this method, A of compound of Formula I is a therapeutic agent that can be used to treat the particular clinical condition to be treated. Some of the cancers that can be treated using compounds of the invention include, but are not limited to, breast cancer, pancreatic cancer, melanoma, prostate cancer, kidney cancer, neuroblastoma, non-Hodgkin's lymphoma, lung cancer, ovarian cancer, colorectal cancer, multiple myeloma, glioblastoma multiforme, and chronic lymphocytic leukemia.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

The following abbreviations are used: Ac: acetyl; Boc: tert-butyloxycarbonyl; BOP: (benzotriazol-1-yloxy)-tris(di-methylamino) phosphonium hexafluorophosphate; Bz: benzoyl; Bzl: benzyl; Dab: 1,4-diaminobutyric acid; Dap: 1,3-diaminopropionic acid; DCC: dicyclohexyl-carbodiimide; DCM: dichloromethane; DIC: diisopropyl carbodiimide; DIEA: diisopropyl-ethylamine; DMAP: 4-(N,N-dimethyl-amino)pyridine; DMF: N,N-dimethyl formamide; DMSO: dimethyl-sulfoxide; EDT: 1,2-ethane-dithiol; Et: ethyl; Fmoc: 9-fluor-enylmethoxy carbonyl; HATU: N-[(dimethylamino)-1H-1,2,3-triazolo[4,5-b]pyridin-1-ylmethylene]-N-methylmethanaminium hexafluorophosphate N-oxide; HBTU: O-benzo-triazolyl-N,N,N',N'-tetramethyluronium hexafluorophosphate; HCTU: 1H-benzotriazo-lium 1-[bis(dimethylamino)methylene]-5-chloro-3-oxide hexafluoro-phosphate; HOBt: hydroxybenzotriazole; hCys: homocysteine; iPr: isopropyl; IPA: isopropyl alcohol; Me: methyl; Mmt: 4-mthoxytrityl; Mpa: 3-mercaptopropionic acid; 2Nal: 2-naphthylalanine; 1Nal: 1-naphthylalanine; NMM: N-methylmorpholine; NMP: N-methyl-pyrrolidone; Orn: ornithine; Pbf: 2,2,4,6,7-pentamethyl-dihydrobenzofurane-5-sulfonyl; PBS: phosphate buffered saline; PyBOP: (benzotriazol-1-yloxy)-tris(pyrrolidino)-phosphonium hexafluoro-phosphate; PyBrOP: bromotris(pyrrolidino) phosphonium hexafluorophosphate; tBu: tert-butyl; TFA: trifluoroacetic acid; TFE: trifluroethanol; THF: tetrahydro-furan; TIS: triisopropyl silane; Trt: trityl; mini-PEG6: 6-mer of ethylene glycol; all common amino acids are expressed as three letter symbols or otherwise specified.

Mass Spectroscopy (MS) Analysis:

Preparation of compounds of the present invention as described in the following examples is meant to be illustrative rather than limiting. In each of these examples, the observed molecular weight is reported as a de-convoluted value. The de-convoluted value is derived from the formula MW (observed)=n(m/z)-n, where m/z represents the charged ion (positive mode) and n is the number of charges of the specific species. When multiple charged species are present in the mass spectrum, the observed molecular weight is reported as an average.

General Method of Peptide Synthesis, Cyclic Structure Formation, and Salt Exchange:

Peptides were synthesized using solid phase peptide synthesis chemistry known in the art. The cyclic structure of those peptides was established, for a disulfide, by using air oxidation, or iodine oxidation in the presence of acidic acid, or for a bisthioether ring, by nucleophilic substitution using a bis(halomethyl) aryl compound, typically using 1.3 equivalents of a bis(bromomethyl) aryl compound, in the presence of a base, such as 15 mM ammonium bicarbonate solution.

Isotopic or radioactive labeled acetones are commercially available from various vendors. If there is a need for custom preparation of isotopic or radioactive labeled acetones, methods can be found in known arts, for example Rolf Voges, et al., *Preparation of Compounds Labeled with Tritium and Carbon*-14 (John Wiley & Sons (2009).

Preparation of peptide-drug conjugates with various linkers is known in the art (G. T. Hermanson, *Bioconjugate Techniques*, 2$^{nd}$ Ed., Academic Press Elsevier, 2008). For example, a procedure on conjugation (i.e., linkage or attachment of peptide) through thiol of cysteine side chain has been reported by Backer and coworkers (M. V. Backer, et al., pp 275-294 in *Methods in Molecular Biology*, vol. 494: *Peptide-Based Drug Design*, edited by L. Otvos, Humana Press, New York, N.Y., 2008).

Paclitaxel Activation—

Preparation of 2'-maleimide-paclitaxel: Dissolving one gram of paclitaxel (1.2 mmoles) in 160 mL of DCM, adding 0.12 mmole of DMAP and cooling the reaction mixture to 0° C. To the cooled reaction mixture, was added 2.4 mmoles of 3-maleimidopropionic acid, and followed by 1.2 mmoles of DIC under stirring. The reaction mixture was then slowly warmed up to room temperature and the coupling reaction was allowed to proceed at room temperature for 18 h under continuous stirring. Crude product of 2'-maleimide-paclitaxel was purified to a purity >90% and used for conjugation to a cyclic CXCR4 antagonist peptide.

Most of the drugs disclosed herein as a cancer therapy to be conjugated to the high affinity CXCR4 binding ligand peptide conjugate can be activated and incorporated in a similar way known to the person of the art.

Purification, Salt Form Conversion, and Final Product Characterization:

Final products were purified by reverse phased HPLC and further characterized by analytical HPLC and mass spectroscopy. Peptides purified from reverse phased HPLC were usually in trifluoroacetic acid (TFA) form. This salt was typically converted to a more pharmaceutically friendly salt form, such as acetic acid or hydrochloric acid salt form. Converting a peptide in TFA salt to a hydrochloric acid salt could be achieved by repeated lyophilization of the peptide in TFA salt in a dilute hydrochloric acid solution. For conversion of a peptide in TFA salt to an acetate salt, typically the following process was used. Strong anion exchange resin (chloride form, substitution 3 mmole/g, water content 50%, using 2 grams of resin per gram of peptide) was first washed three times with milli Q water, then three times with 1 N NaOH solution three times, 5 min/time, and then five times with milli Q water, 5 min/time. The resin was further washed with 75% ethanol water until the pH reaches about 7.4. This resin was treated with 10% acetic acid solution three times, five minutes each time. The resin was then washed with 1% acetic acid solution three times, five minutes each time. The resin was ready for the salt conversion of the purified peptide.

The purified, lyophilized peptide was dissolved in 1% acetic acid solution and added to the prepared resin described above. The mixture was agitated or magnetically stirred at room temperature for 1 h. The supernatant was separated. The resin was washed three times with 1% acetic acid solution. The supernatant and the washing solution were combined, filtered through a 0.22 mm membrane and lyophilized, to afford a peptide in acetate salt.

Example 1: Synthesis of (MLB-1707)

Peptide Chain Assembly:

The peptide chain of Cys(Mmt)-Tyr(tBu)-Lys(iPr,Boc)-(D-Arg(Pbf))-2Nal-Gly-Cys(Mmt)-Lys(iPr,Boc)-(mini-PEG6)-Cys(Trt) (SEQ ID NO:8) was assembled by standard Fmoc chemistry using Rink AM resin. Briefly, 0.8 g of Rink AM resin was swollen in DCM for 14 h and then washed four times with DMF. Removal of Fmoc was carried out in 20% piperidine in DMF for 20 min at room temperature and washed several times with DMF. Ninhydrin test was negative. Stepwise chain assembly started with Fmoc-Cys(Trt)-OH from the C-terminal end of the linear peptide. Three equivalents of protected amino acid Fmoc-Cys(Trt)-OH were activated with DIC/HOBt in DMF, and coupled to the Fmoc-removed Rink AM resin prepared above for 2 h at room temperature. Ninhydrin test was negative. Capping of the non-reacted amino group was performed for 30 min with 5 mL of a mixture of acetic anhydride/DIEA/DCM at a volume ratio of 1:1:2. This was followed by Fmoc removal using 20% piperidine in DMF for 20 min. The following residues were coupled sequentially without capping: Fmoc-mini-PEG6-OH, Fmoc-Lys(iPr,Boc)-OH, Fmoc-Cys(Mmt)-OH, Fmoc-Gly-OH, Fmoc-2Nal-OH, Fmoc-D-Arg(Pbf))-OH, Fmoc-Lys(iPr,Boc)-OH, Fmoc-Tyr(tBu)-OH, and Fmoc-Cys(Mmt)-OH. After the coupling of last residue Fmoc-Cys(Mmt), Fmoc protection was removed again using 20% piperidine in DMF for 20 min. N-terminal acetylation was carried out with 5 mL of a mixture of acetic anhydride/DIEA/DMF (1:1:4, v/v/v) for 30 min at room temperature. The resin was then washed with DMF three time and then with DCM twice, dried under vacuum.

Removal of Mmt Protection on Cys Residues and Cyclization on Solid Phase:

Using 30 mL of a cleavage cocktail (TFA/EDT/TIS/DCM, 3:1.5:1.5:100, v/v) per gram of resin, Mmt protection of Cys side chain was removed. This deprotection procedure was repeated three times, 10 min each time at room temperature. The resin was then washed three time with DCM and ten times with DMF, to make sure complete removal of the residual TFA. To the well washed resin, add 10 mL of DMF and 2 mL of DIEA per gram of resin, followed by slow, dropwise addition of 1.2 eq of 1,2-bis(bromomethyl)benzene. The cyclization reaction was allowed to proceed for 1 h at room temperature. Test cleavage and MS confirmed the completion of cyclization. The reaction mixture was then drained from the resin, and the resin was further washed three times with DMF and twice with DCM. The resin was then dried under vacuum before cleavage.

Peptide cleavage from solid support and side chain deprotection:

The finished peptide was deprotected and cleaved from the dry resin using a cleavage cocktail (TFA/EDT/TIS/$H_2O$/thioanisole/phenol, per 100 mL of solution contains 81.5 mL TFA, 2.5 mL EDT, 1.0 mL TIS, 5.0 mL $H_2O$, 5.0 mL thioanisole, and 5.0 grams phenol) at 10 mL/gram of resin, for 70 min at room temperature. The resin was removed by filtration and washed a few milliliters of cleavage cocktail. To the cleavage mixture was added eight volumes of methyl t-butyl ether. The crude peptide precipitates were separated by centrifugation at 3000 rpm for 3 min. The crude peptide precipitates were washed three times with methyl t-butyl ether. The crude peptide was purified to a purity >90% on preparative HPLC, and lyophilized.

Conjugation of Paclitaxel:

The purified cyclic peptide was mixed with 2'-maleimide-paclitaxel previous prepared at a 1:1.2 molar ratio, and added 30% aqueous acetonitrile to give a final peptide concentration of 10 mg/mL. A solution of 0.5 mole/L $NH_4HCO_3$ was used to adjust the reaction mixture to pH 7.5. The conjugation reaction was completed in about half an hour as confirmed by MS. The final product was purified using a reverse-phased preparative column Daisogel (50× 250 mm, 8 mm); mobile phases—Solvent A: 0.1% TFA water; Solvent B: 0.1% TFA acetonitrile. Fractions containing the target product were combined and lyophilized (a TFA salt).

Salt exchange as described above afforded a peptide in acetate salt. Analytical HPLC purity of the final peptide product 95.14%; MW cal.: 2725.56; MW obs.: 2724.75.

Example 2: Synthesis of (MLB-1708)

Peptide Chain Assembly:

The peptide chain of Cys(Trt)-Cys(Mmt)-Tyr(tBu)-Lys(iPr,Boc)-(D-Arg(Pbf))-2Nal-Gly-Cys(Mmt)-Lys(iPr,Boc)-Gly (SEQ ID NO:9) was assembled by standard Fmoc chemistry using Rink AM resin. Briefly, 3.6 g of Rink AM resin was swollen in DCM for 14 h and then washed four times with DMF. Removal of Fmoc was carried out in 20% piperidine in DMF for 20 min at room temperature and washed several times with DMF. Ninhydrin test was negative. Stepwise chain assembly started with Fmoc-Gly-OH from the C-terminal end of the linear peptide. Three equivalents of protected amino acid Fmoc-Gly-OH were activated with DIC/HOBt in DMF, and coupled to the Fmoc-removed Rink AM resin prepared above for 2 h at room temperature. Ninhydrin test was negative. Capping of the non-reacted amino group was performed for 30 min with 20 mL of a mixture of acetic anhydride/DIEA/DCM at a volume ratio of 1:1:2. This was followed by Fmoc removal using 20% piperidine in DMF for 20 min. The following residues were coupled sequentially without capping: Fmoc-Lys(iPr,Boc)-OH, Fmoc-Cys(Mmt)-OH, Fmoc-Gly-OH, Fmoc-2Nal-OH, Fmoc-D-Arg(Pbf))-OH, Fmoc-Lys(iPr,Boc)-OH, Fmoc-Tyr(tBu)-OH, Fmoc-Cys(Mmt)-OH, and Fmoc-Cys(Trt)-OH. After the coupling of last residue Fmoc-Cys(Trt)-OH, Fmoc protection was removed again using 20% piperidine in DMF for 20 min. N-terminal acetylation was carried out with 20 mL of a mixture of acetic anhydride/DIEA/DMF (1:1:4, v/v/v) for 30 min at room temperature. The resin was then washed with DMF three time and then with DCM twice, dried under vacuum.

Removal of Mmt Protection on Cys Residues and Cyclization on Solid Phase:

Using 30 mL of a cleavage cocktail (TFA/EDT/TIS/DCM, 3:1.5:1.5:100, v/v) per gram of resin, Mmt protection of Cys side chain was removed. The deprotection procedure was repeated three times, 10 min each time at room temperature. The resin was then washed three time with DCM and ten times with DMF, to make sure the complete removal of residual TFA. To the well washed resin, was added 10 mL of DMF and 2 mL of DIEA per gram of resin. The cyclization reaction was allowed to proceed for 1 h at room temperature. Test cleavage and MS confirmed the completion of cyclization. The reaction mixture was then drained from the resin, and the resin was further washed three times with DMF and twice with DCM. The resin was then dried under vacuum before cleavage.

Peptide Cleavage from Solid Support and Side Chain Deprotection:

The finished peptide was deprotected and cleaved from the dry resin using a cleavage cocktail (TFA/EDT/TIS/H$_2$O/thioanisole/phenol, per 100 mL of solution contains 81.5 mL TFA, 2.5 mL EDT, 1.0 mL TIS, 5.0 mL H$_2$O, 5.0 mL thioanisole, and 5.0 grams phenol) at 10 mL/gram of resin, for 70 min at room temperature. The resin was removed by filtration and washed a few milliliters of cleavage cocktail. To the cleavage mixture was added eight volumes of methyl t-butyl ether. The crude peptide precipitates were separated by centrifugation at 3000 rpm for 3 min. The crude peptide precipitates were washed three times with methyl t-butyl ether. The crude peptide was purified to a purity >90% on preparative HPLC, and lyophilized.

Conjugation of Paclitaxel:

The purified cyclic peptide was mixed with 2'-maleimide-paclitaxel previous prepared at a 1:1.2 molar ratio, and added 30% aqueous acetonitrile to give a final peptide concentration of 10 mg/mL. A solution of 0.5 mole/L NH$_4$HCO$_3$ was used to adjust the reaction mixture to pH 7.5. The conjugation reaction was completed in about half an hour as confirmed by MS. The final product was purified using a reverse-phased preparative column Daisogel (50× 250 mm, 8 mm); mobile phases—Solvent A: 0.1% TFA water; Solvent B: 0.1% TFA acetonitrile. Fractions containing the target product were combined and lyophilized (a TFA salt).

Salt exchange as described above afforded a peptide in acetate salt. Analytical HPLC purity of the final peptide product 95.71%; MW cal.: 2343.70; MW obs.: 2342.85.

Example 3: Synthesis of (MLB-1710)

Peptide Chain Assembly:

The peptide chain of Cys(Trt)-Cys(Mmt)-Tyr(tBu)-Lys(iPr,Boc)-(D-Arg(Pbf))-2Nal-Gly-Cys(Mmt)-Lys(iPr,Boc)-Gly (SEQ ID NO:9) was assembled by standard Fmoc chemistry using Rink AM resin. Briefly, 3.6 g of Rink AM resin was swollen in DCM for 14 h and then washed four times with DMF. Removal of Fmoc was carried out in 20% piperidine in DMF for 20 min at room temperature and washed several times with DMF. Ninhydrin test was negative. Stepwise chain assembly started with Fmoc-Gly-OH from the C-terminal end of the linear peptide. Three equivalents of protected amino acid Fmoc-Gly-OH were activated with DIC/HOBt in DMF, and coupled to the Fmoc-removed Rink AM resin prepared above for 2 h at room temperature. Ninhydrin test was negative. Capping of the non-reacted amino group was performed for 30 min with 20 mL of a mixture of acetic anhydride/DIEA/DCM at a volume ratio of 1:1:2. This was followed by Fmoc removal using 20% piperidine in DMF for 20 min. The following residues were coupled sequentially without capping: Fmoc-Lys(iPr,Boc)-OH, Fmoc-Cys(Mmt)-OH, Fmoc-Gly-OH, Fmoc-2Nal-OH, Fmoc-D-Arg(Pbf))-OH, Fmoc-Lys(iPr,Boc)-OH, Fmoc-Tyr(tBu)-OH, Fmoc-Cys(Mmt)-OH, and Fmoc-Cys(Trt)-OH. After the coupling of last residue Fmoc-Cys(Trt)-OH, Fmoc protection was removed again using 20% piperidine in DMF for 20 min. N-terminal acetylation was carried out with 20 mL of a mixture of acetic anhydride/DIEA/DMF (1:1:4, v/v/v) for 30 min at room temperature. The resin was then washed with DMF three time and then with DCM twice, dried under vacuum.

Removal of Mmt Protection on Cys Residues and Cyclization on Solid Phase:

Using 30 mL of a cleavage cocktail (TFA/EDT/TIS/DCM, 3:1.5:1.5:100, v/v) per gram of resin, Mmt protection of Cys side chain was removed. The deprotection procedure was repeated three times, 10 min each time at room temperature. The resin was then washed three time with DCM and ten times with DMF, to make sure complete removal of the residual TFA. To the well washed resin, add 10 mL of DMF and 2 mL of DIEA per gram of resin, followed by slow, dropwise addition of 1.2 eq of 1,2-bis(bromomethyl)benzene. The cyclization reaction was allowed to proceed for 1 h at room temperature. Test cleavage and MS confirmed the completion of cyclization. The reaction mixture was then drained from the resin, and the resin was further washed three times with DMF and twice with DCM. The resin was then dried under vacuum before cleavage.

Peptide Cleavage from Solid Support and Side Chain Deprotection:

The finished peptide was deprotected and cleaved from the dry resin using a cleavage cocktail (TFA/EDT/TIS/H$_2$O/thioanisole/phenol, per 100 mL of solution contains 81.5 mL TFA, 2.5 mL EDT, 1.0 mL TIS, 5.0 mL H$_2$O, 5.0 mL thioanisole, and 5.0 grams phenol) at 10 mL per gram of resin, for 70 min at room temperature. The resin was removed by filtration and washed with a few milliliters of cleavage cocktail. To the cleavage mixture was added eight volumes of methyl t-butyl ether. The crude peptide precipitates were separated by centrifugation at 3000 rpm for 3 min. The crude peptide precipitates were washed three times with methyl t-butyl ether. The crude peptide was purified to a purity >90% on preparative HPLC, and lyophilized.

Conjugation of Paclitaxel:

The purified cyclic peptide was mixed with 2'-maleimide-paclitaxel previous prepared at a 1:1.2 molar ratio, and added 30% aqueous acetonitrile to give a final peptide concentration of 10 mg/mL. A solution of 0.5 mole/L $NH_4HCO_3$ was used to adjust the reaction mixture to pH 7.5. The conjugation reaction was completed in about half an hour as confirmed by MS. The final product was purified using a reverse-phased preparative column Daisogel (50× 250 mm, 8 mm); mobile phases—Solvent A: 0.1% TFA water; Solvent B: 0.1% TFA acetonitrile. Fractions containing the target product were combined and lyophilized (a TFA salt).

Salt exchange as described above afforded a peptide in acetate salt. Analytical HPLC purity of the final peptide product 95.07%; MW cal.: 2446.96; MW obs.: 2446.50.

Example 4: Synthesis of (MLB-1711)

Peptide Chain Assembly:

The peptide chain of Cys(Trt)-(mini-PEG6)-Cys(Mmt)-Tyr(tBu)-Lys(iPr,Boc)-(D-Arg(Pbf))-2Nal-Gly-Cys(Mmt)-Lys(iPr,Boc)-Gly (SEQ ID NO:10) was assembled by standard Fmoc chemistry using Rink AM resin. Briefly, 3.6 g of Rink AM resin was swollen in DCM for 14 h and then washed four times with DMF. Removal of Fmoc was carried out in 20% piperidine in DMF for 20 min at room temperature and washed several times with DMF. Ninhydrin test was negative. Stepwise chain assembly started with Fmoc-Gly-OH from the C-terminal end of the linear peptide. Three equivalents of protected amino acid Fmoc-Gly-OH were activated with DIC/HOBt in DMF, and coupled to the Fmoc-removed Rink AM resin prepared above for 2 h at room temperature. Ninhydrin test was negative. Capping of the non-reacted amino group was performed for 30 min with 20 mL of a mixture of acetic anhydride/DIEA/DCM at a volume ratio of 1:1:2. This was followed by Fmoc removal using 20% piperidine in DMF for 20 min. The following residues were coupled sequentially without capping: Fmoc-Lys(iPr,Boc)-OH, Fmoc-Cys(Mmt)-OH, Fmoc-Gly-OH, Fmoc-2Nal-OH, Fmoc-D-Arg(Pbf))-OH, Fmoc-Lys(iPr, Boc)-OH, Fmoc-Tyr(tBu)-OH, Fmoc-Cys(Mmt)-OH, Fmoc-(mini-PEG6)-OH, and Fmoc-Cys(Trt)-OH. After the coupling of last residue Fmoc-Cys(Trt)-OH, Fmoc protection was removed again using 20% piperidine in DMF for 20 min. N-terminal acetylation was carried out with 20 mL of a mixture of acetic anhydride/DIEA/DMF (1:1:4, v/v/v) for 30 min at room temperature. The resin was then washed with DMF three time and then with DCM twice, dried under vacuum.

Removal of Mmt Protection on Cys Residues and Cyclization on Solid Phase:

Using 30 mL of a cleavage cocktail (TFA/EDT/TIS/DCM, 3:1.5:1.5:100, v/v) per gram of resin, Mmt protection of Cys side chain was removed. The deprotection procedure was repeated three times, 10 min each time at room temperature. The resin was then washed three time with DCM and ten times with DMF, to make sure the complete removal of residual TFA. To the well washed resin, was added 10 mL of DMF and 2 mL of DIEA per gram of resin, followed by slow, dropwise addition of 1.2 eq of 1,2-bis(bromomethyl) benzene. The cyclization reaction was allowed to proceed for 1 h at room temperature. Test cleavage and MS confirmed the completion of cyclization. The reaction mixture was then drained from the resin, and the resin was further washed three times with DMF and twice with DCM. The resin was then dried under vacuum before cleavage.

Peptide Cleavage from Solid Support and Side Chain Deprotection:

The finished peptide was deprotected and cleaved from the dry resin using a cleavage cocktail (TFA/EDT/TIS/$H_2O$/thioanisole/phenol, per 100 mL of solution contains 81.5 mL TFA, 2.5 mL EDT, 1.0 mL TIS, 5.0 mL $H_2O$, 5.0 mL thioanisole, and 5.0 grams phenol) at 10 mL per gram of resin, for 70 min at room temperature. The resin was removed by filtration and washed with a few milliliters of cleavage cocktail. To the cleavage mixture was added eight volumes of methyl t-butyl ether. The crude peptide precipitates were separated by centrifugation at 3000 rpm for 3 min. The crude peptide precipitates were washed three times with methyl t-butyl ether. The crude peptide was purified to a purity >90% on preparative HPLC, and lyophilized.

Conjugation of Paclitaxel:

The purified cyclic peptide was mixed with 2'-maleimide-paclitaxel previous prepared at a 1:1.2 molar ratio, and added 30% aqueous acetonitrile to give a final peptide concentration of 10 mg/mL. A solution of 0.5 mole/L $NH_4HCO_3$ was used to adjust the reaction mixture to pH 7.5. The conjugation reaction was completed in about half an hour as confirmed by MS. The final product was purified using a reverse-phased preparative column Daisogel (50× 250 mm, 8 mm); mobile phases—Solvent A: 0.1% TFA water; Solvent B: 0.1% TFA acetonitrile. Fractions containing the target product were combined and lyophilized (a TFA salt).

Salt exchange as described above afforded a peptide in acetate salt. Analytical HPLC purity of the final peptide product 95.10%; MW cal.: 2781.25; MW obs.: 2781.75.

Example 5: Synthesis of (MLB-1713)

Peptide Chain Assembly:

The peptide chain of Phe-Tyr(tBu)-Lys(iPr,Boc)-(D-Arg(Pbf))-2Nal-Gly-(D-Glu(OAll)-Lys(iPr,Boc)-(mini-PEG6)-Cys(Trt)-Gly (SEQ ID NO:11) was assembled by standard Fmoc chemistry using Rink AM resin. Briefly, 1.0 g of Rink AM resin was swollen in DCM for 14 h and then washed four times with DMF. Removal of Fmoc was carried out in 20% piperidine in DMF for 20 min at room temperature and washed several times with DMF. Ninhydrin test was negative. Stepwise chain assembly started with Fmoc-Gly-OH from the C-terminal end of the linear peptide. Three equivalents of protected amino acid Fmoc-Gly-OH were activated with DIC/HOBt in DMF, and coupled to the Fmoc-removed Rink AM resin prepared above for 2 h at room temperature. Ninhydrin test was negative. Capping of the non-reacted amino group was performed for 30 min with 6 mL of a mixture of acetic anhydride/DIEA/DCM at a volume ratio of 1:1:2. This was followed by Fmoc removal using 20% piperidine in DMF for 20 min. The following residues were coupled sequentially without capping: Fmoc-Cys(Trt)-OH, Fmoc-(mini-PEG6)-OH, Fmoc-Lys(iPr,Boc)-OH, Fmoc-D-Glu(OAll)-OH, Fmoc-Gly-OH, Fmoc-2Nal-OH, Fmoc-D-Arg(Pbf))-OH, Fmoc-Lys(iPr,Boc)-OH, Fmoc-Tyr(tBu)-OH, and Fmoc-Phe-OH. After the coupling of last residue of Fmoc-Phe-OH, the resin was then washed with DMF three time. Fmoc protection group of Phe was not removed at this stage.

Removal of OAll Protection, Removal of Fmoc Protection, and Cyclization on Solid Phase:

The allyl ester side chain protection of D-Glu was removed with 0.1 equivalent of Pd(Ph$_3$P)$_4$ in the presence of 24 equivalents of phenylsilane in dichloromethane. This process was repeated once for complete removal of the allyl side chain deprotection. Then the Fmoc protection group at the N-terminus was removed with 20% piperidine in DMF for 20 min. The deprotected side chain carboxylic acid of D-Glu was then activated with PyBOP ((benzotriazol-1-yloxy)-tris(pyrrolidino)-phosphonium hexafluorophosphate)/DIEA and cyclized to the alpha amino group of Phe residue on resin. The cyclization was completed within 2 h, as confirmed by MS after a test cleavage.

Peptide Cleavage from Solid Support and Side Chain Deprotection:

The finished peptide was deprotected and cleaved from the dry resin using a cleavage cocktail (TFA/EDT/TIS/H$_2$O/thioanisole/phenol, per 100 mL of solution contains 81.5 mL TFA, 2.5 mL EDT, 1.0 mL TIS, 5.0 mL H$_2$O, 5.0 mL thioanisole, and 5.0 grams phenol) at 10 mL per gram of resin, for 70 min at room temperature. The resin was removed by filtration and washed with a few milliliters of cleavage cocktail. To the cleavage mixture was added eight volumes of methyl t-butyl ether. The crude peptide precipitates were separated by centrifugation at 3000 rpm for 3 min. The crude peptide precipitates were washed three times with methyl t-butyl ether. The crude peptide was purified to a purity >90% on preparative HPLC, and lyophilized.

Conjugation of Paclitaxel:

The purified cyclic peptide was mixed with 2'-maleimide-paclitaxel previous prepared at a 1:1.2 molar ratio, and added 30% aqueous acetonitrile to give a final peptide concentration of 10 mg/mL. A solution of 0.5 mole/L NH$_4$HCO$_3$ was used to adjust the reaction mixture to pH 7.5. The conjugation reaction was completed in about half an hour as confirmed by MS. The final product was purified using a reverse-phased preparative column Daisogel (50× 250 mm, 8 mm); mobile phases—Solvent A: 0.1% TFA water; Solvent B: 0.1% TFA acetonitrile. Fractions containing the target product were combined and lyophilized (a TFA salt).

Salt exchange as described above afforded a peptide in acetate salt. Analytical HPLC purity of the final peptide product 95.03%; MW cal.: 2690.40; MW obs.: 2690.25.

Example 6: Synthesis of (MLB-1703)

Peptide Chain Assembly:

The peptide chain of Cys(Mmt)-Tyr(tBu)-Lys(iPr,Boc)-(D-Arg(Pbf))-2Nal-Gly-Cys(Mmt)-Lys(iPr,Boc)-Gly-Cys (Trt) (SEQ ID NO:12) was assembled by standard Fmoc chemistry using Rink AM resin. Briefly, 0.8 g of Rink AM resin was swollen in DCM for 14 h and then washed four times with DMF. Removal of Fmoc was carried out in 20% piperidine in DMF for 20 min at room temperature and washed several times with DMF. Ninhydrin test was negative. Stepwise chain assembly started with Fmoc-Cys(Trt)-OH from the C-terminal end of the linear peptide. Three equivalents of protected amino acid Fmoc-Cys(Trt)-OH were activated with DIC/HOBt in DMF, and coupled to the Fmoc-removed Rink AM resin prepared above for 2 h at room temperature. Ninhydrin test was negative. Capping of the non-reacted amino group was performed for 30 min with 5 mL of a mixture of acetic anhydride/DIEA/DCM at a volume ratio of 1:1:2. This was followed by Fmoc removal using 20% piperidine in DMF for 20 min. The following residues were coupled sequentially without capping: Fmoc-Gly-OH, Fmoc-Lys(iPr,Boc)-OH, Fmoc-Cys(Mmt)-OH, Fmoc-Gly-OH, Fmoc-2Nal-OH, Fmoc-D-Arg(Pbf))-OH, Fmoc-Lys(iPr,Boc)-OH, Fmoc-Tyr(tBu)-OH, and Fmoc-Cys(Mmt)-OH. After the coupling of last residue Fmoc-Cys(Mmt)-OH, Fmoc protection was removed again using 20% piperidine in DMF for 20 min. N-terminal acetylation was carried out with 5 mL of a mixture of acetic anhydride/DIEA/DMF (1:1:4, v/v/v) for 30 min at room temperature. The resin was then washed with DMF three time and then with DCM twice, dried under vacuum.

Removal of Mmt Protection on Cys Residues and Cyclization on Solid Phase:

Using 30 mL of a cleavage cocktail (TFA/EDT/TIS/DCM, 3:1.5:1.5:100, v/v) per gram of resin, Mmt protection of Cys side chain was removed. The deprotection procedure was repeated three times, 10 min each time at room temperature. The resin was then washed three time with DCM and ten times with DMF, to make sure the complete removal of residual TFA. To the well washed resin, add 10 mL of DMF and 2 mL of DIEA per gram of resin, followed by slow, dropwise addition of 1.2 eq of 1,2-bis(bromomethyl) benzene. The cyclization reaction was allowed to proceed for 1 h at room temperature. Test cleavage and MS confirmed the completion of cyclization. The reaction mixture was then drained from the resin, and the resin was further washed three times with DMF and twice with DCM. The resin was then dried under vacuum before cleavage.

Peptide Cleavage from Solid Support and Side Chain Deprotection:

The finished peptide was deprotected and cleaved from the dry resin using a cleavage cocktail (TFA/EDT/TIS/H$_2$O/thioanisole/phenol, per 100 mL of solution contains 81.5 mL TFA, 2.5 mL EDT, 1.0 mL TIS, 5.0 mL H$_2$O, 5.0 mL thioanisole, and 5.0 grams phenol) at 10 mL per gram of resin, for 70 min at room temperature. The resin was removed by filtration and washed with a few milliliters of cleavage cocktail. To the cleavage mixture was added eight volumes of methyl t-butyl ether. The crude peptide precipitates were separated by centrifugation at 3000 rpm for 3 min. The crude peptide precipitates were washed three times with methyl t-butyl ether. The crude peptide was purified to a purity >90% on preparative HPLC, and lyophilized.

Conjugation of Paclitaxel:

The purified cyclic peptide was mixed with 2'-maleimide-paclitaxel previous prepared at a 1:1.2 molar ratio, and added 30% aqueous acetonitrile to give a final peptide concentration of 10 mg/mL. A solution of 0.5 mole/L NH$_4$HCO$_3$ was used to adjust the reaction mixture to pH 7.5. The conjugation reaction was completed in about half an hour as confirmed by MS. The final product was purified using a reverse-phased preparative column Daisogel (50× 250 mm, 8 mm); mobile phases—Solvent A: 0.1% TFA water; Solvent B: 0.1% TFA acetonitrile. Fractions containing the target product were combined and lyophilized (a TFA salt).

Salt exchange as described above afforded a peptide in acetate salt. Analytical HPLC purity of the final peptide product 95.13%; MW cal.: 2447.86; MW obs.: 2446.95.

Human CXCR4/$^{125}$I-SDF-1α Binding Inhibition Assay:

(Performed by EUROFINS CEREP SA, Le Bois l'Eveque, 86600 Celle L'Evescault, France): Human chemokine receptor CXCR4 expressed in Chem-1 cells were used in modified HEPES buffer pH 7.4. A 0.5 μg (Membrane protein may change from lot to lot, the concentration used will be adjusted if necessary), aliquot was incubated with 0.03 nM [$^{125}$I]SDF-1α for 90 minutes at 25° C. Non-specific binding was estimated in the presence of 30 nM SDF-1α. Membranes were filtered and washed, filters were then counted to determine [$^{125}$I]SDF-1α specifically bound. Compounds were screened starting at 10 µM with 11-point dilutions (Valenzuela-Fernandez A, et al. *J Biol Chem.* 277(18):15677, 2002). The CXCR4 binding data together with their physical characterizations are shown in the table below.

TABLE 1

Characterization and Binding Activities of the illustrative Peptides

| Example No. | MLB No. | Cal. MW (Da) | Obs. MW (Da) | HPLC purity (%) | CXCR4 IC$_{50}$ (nM) | CXCR4 K$_b$ (nM) |
|---|---|---|---|---|---|---|
| 1 | MLB-1707 | 2725.56 | 2724.75 | 95.14 | 2.30 | 0.70 |
| 2 | MLB-1708 | 2343.70 | 2342.85 | 95.71 | 9.40 | 2.80 |
| 3 | MLB-1710 | 2446.96 | 2446.50 | 95.07 | 16.0 | 4.90 |
| 4 | MLB-1711 | 2781.25 | 2781.75 | 95.10 | 3.90 | 1.20 |
| 5 | MLB-1713 | 2690.40 | 2690.25 | 95.03 | 0.96 | 0.29 |
| 6 | MLB-1703 | 2447.86 | 2446.95 | 95.13 | n/a* | n/a* |

*n/a: not available.

In addition to the high affinity CXCR4 binding ligand peptide drug conjugates disclosed herein, preparation and characterization of other high affinity CXCR4 binding ligand peptides can be found in U.S. Provisional Patent Applications: 62/384,132, filed Sep. 6, 2016, and 62/505,064, filed May 11, 2017 (See Table 2 below).

Isotopic or radioactive labeled acetones are commercially available from various vendors. If there is a need for custom preparation of isotopic or radioactive labeled acetones, methods can be found in known arts, for example Rolf Voges, et al., *Preparation of Compounds Labeled with Tritium and Carbon-14* (*John Wiley & Sons* (2009).

Preparation of peptide-drug conjugates with various linkers are known in the art (G. T. Hermanson, *Bioconjugate Techniques*, 2$^{nd}$ Ed., Academic Press Elsevier, 2008). An example of a process for preparing peptide conjugates (e.g., linkage or attachment of an active component to a peptide) through thiol of cysteine side chain is disclosed in Backer, et al., pp 275-294 in *Methods in Molecular Biology*, vol. 494: *Peptide-Based Drug Design*, edited by L. Otvos, Humana Press, New York, N.Y., 2008.

TABLE 2

Other High Affinity CXCR4 Binding Ligand Peptides

| Entry | MLB No. | Cal. MW (Da) | Obs. MW (Da) | HPLC purity (%) | CXCR4 IC$_{50}$ (nM) | Binding K$_b$ (nM) |
|---|---|---|---|---|---|---|
| 1 | MLB-001 | 1353.49 | 1353.45 | 96.64 | 24.0 | 7.3 |
| 2 | MLB-002 | 1366.93 | 1367.70 | 98.78 | 0.92 | 0.28 |
| 3 | MLB-003 | 1381.35 | 1381.80 | 98.14 | 0.98 | 0.30 |
| 4 | MLB-004 | 1366.83 | 1367.25 | 97.02 | 0.70 | 0.21 |
| 5 | MLB-005 | 1353.49 | 1353.00 | 96.05 | >>1000 | >>1000 |
| 6 | MLB-006 | 1408.69 | 1409.10 | 96.54 | 1.50 | 0.45 |
| 7 | MLB-007 | 1204.51 | 1205.25 | 95.71 | 0.64 | 0.19 |
| 8 | MLB-008 | 1430.43 | 1431.00 | 96.44 | 0.95 | 0.29 |
| 9 | MLB-009 | 1451.84 | 1452.60 | 96.38 | 0.61 | 0.18 |
| 10 | MLB-010 | 1247.61 | 1248.00 | 96.13 | 0.56 | 0.17 |
| 11 | MLB-021 | 1310.64 | 1310.70 | 95.98 | 0.42 | 0.13 |
| 12 | MLB-022 | 1310.64 | 1310.55 | 95.64 | 0.71 | 0.21 |
| 13 | MLB-023 | 1296.61 | 1296.75 | 97.04 | 3.40 | 1.00 |
| 14 | MLB-024 | 1338.69 | 1338.9 | 97.59 | 1.30 | 0.39 |
| 15 | MLB-025 | 1324.67 | 1324.65 | 95.67 | 0.84 | 0.25 |
| 16 | MLB-026 | 1276.62 | 1276.65 | 95.03 | 0.89 | 0.27 |
| 17 | MLB-027 | 1318.70 | 1318.80 | 95.50 | 0.48 | 0.15 |
| 18 | MLB-028 | 1458.97 | 1458.75 | 96.42 | 8.20 | 2.50 |
| 19 | MLB-029 | 1515.08 | 1515.00 | 95.31 | 11.0 | 3.20 |
| 20 | MLB-030 | 1400.76 | 1400.85 | 95.60 | 1.30 | 0.39 |
| 21 | MLB-031 | 1309.69 | 1309.20 | 96.54 | n/a* | n/a* |
| 22 | MLB-032 | 1338.70 | 1338.60 | 97.59 | 0.40 | 0.12 |
| 23 | MLB-033 | 1338.82 | 1338.45 | 95.23 | 3.30 | 0.99 |

*n/a: not available.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. A high affinity CXCR4 selective binding ligand peptide conjugate (PC) of the Formula:

$$P\text{-}(L\text{-}A)_n \qquad \text{I}$$

or a pharmaceutically acceptable salt thereof, wherein
n is an integer from 1 to about 5 or the sum of (the total number of side-chain functional groups within P)
A is one or more diagnostic agents, therapeutic agents, or imaging agents;
L is a bifunctional linker or absent; and
P is a high affinity CXCR4 selective binding peptidyl ligand of the formula:

(SEQ ID NO: 1)

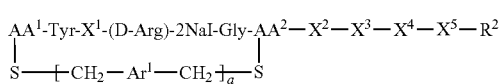

$$AA^1\text{-}Tyr\text{-}X^1\text{-}(D\text{-}Arg)\text{-}2NaI\text{-}Gly\text{-}AA^2\text{-}X^2\text{-}X^3\text{-}X^4\text{-}X^5\text{-}R^2 \qquad \text{II}$$

wherein:
a is 0 or 1;
$AA^1$ along with the sulfur atom that is attached thereto is 3-mercaptopropionic acid, optionally substituted cysteine, or optionally substituted homocysteine;
$AA^2$ along with the sulfur atom that is attached thereto is cysteine or homocysteine;
$Ar^1$ is an optionally substituted aryl;
$X^1$ is Arg, Dap, Dab, Orn, Lys, Dap(iPr), Dab(iPr), Orn(iPr), or Lys(iPr);
$X^2$ is Arg, Dap, Dab, Orn, Lys, Dap(iPr), Dab(iPr), Orn(iPr), Lys(iPr), D-Arg, D-Dap, D-Dab, D-Orn, D-Lys, D-Dap(iPr), D-Dab(iPr), D-Orn(iPr), D-Lys(iPr), or absent;
$X^3$ is Lys, Gly or absent;
$X^4$ is Lys, Phe, 2Nal, 1Nal, the D-isomer thereof, Gly, or absent;
$X^5$ is Lys, Gly or absent; and
$R^2$ is $-OR^4$ or $-NHR^5$, wherein $R^4$ and $R^5$ are H, alkyl, optionally substituted aryl or optionally substituted aralkyl.

2. The high affinity CXCR4 selective binding ligand peptide conjugate of claim 1, wherein A is attached to the N-terminal end or the C-terminal end of said peptide, or to a function group that is present on the side-chain of the amino acid residue of said peptide, or a combination of any one of the positions thereof.

3. The high affinity CXCR4 selective binding ligand peptide conjugate of claim 1, wherein said high affinity CXCR4 selective binding ligand peptide conjugate comprises a plurality of A.

4. The high affinity CXCR4 selective binding ligand peptide conjugate of claim 1, wherein A is an imaging agent.

5. The high affinity CXCR4 selective binding ligand peptide conjugate of claim 1, wherein A is a diagnostic agent.

6. The high affinity CXCR4 selective binding ligand peptide conjugate of claim 1, wherein said diagnostic agent is an imaging agent, an isotopic agent, or a radioactive agent.

7. The high affinity CXCR4 selective binding ligand peptide conjugate of claim 1, wherein said linker comprises a functional group that is capable of releasing A in vivo.

8. The high affinity CXCR4 selective binding ligand peptide conjugate of claim 1, wherein A is a therapeutic agent.

9. The high affinity CXCR4 selective binding ligand peptide conjugate of claim 8, wherein said therapeutic agent is selected from the group consisting of bleomycin, calicheamicin, daunorubicin, docetaxel, doxorubicin, irinotecan, mertansine, monomethyl auristatin E, paclitaxel, SN-38, tesirine, topotecan, tubulysin, *vinca* alkaloids, and an analog or derivative thereof, and a combination thereof.

10. The high affinity CXCR4 selective binding ligand peptide conjugate of claim 1, wherein said high affinity CXCR4 selective binding ligand peptide conjugate is:
cyclo[Phe-Tyr-Lys(iPr)-(D-Arg)-2Nal-Gly-(D-Glu)]-Lys (iPr)-(mini-PEG6)-Cys(S-paclitaxel)-Gly-NH$_2$ (SEQ ID NO:3), wherein the cyclic structure is formed between the α-amino of Phe connected to the side chain of D-Glu; or
$R^a$-cyclo[Cys-Tyr-Lys(iPr)-(D-Arg)-2Nal-Gly-Cys]-Lys(iPr)-$R^b$ (SEQ ID NO:4);
$R^a$-cyclo[hCys-Tyr-Lys(iPr)-(D-Arg)-2Nal-Gly-Cys]-Lys(iPr)-$R^b$ (SEQ ID NO:5);
$R^a$-cyclo[Cys-Tyr-Lys(iPr)-(D-Arg)-2Nal-Gly-hCys]-Lys(iPr)-$R^b$ (SEQ ID NO:6); and (SEQ ID NO: 7)

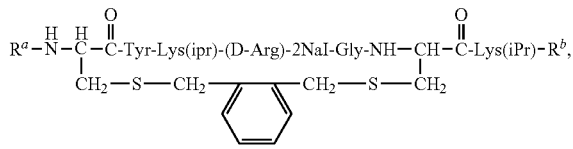

wherein
$R^a$ is acetyl-, acetyl-Cys(S-paclitaxel)-, or acetyl-Cys(S-paclitaxel)-(mini-PEG6)-; and
$R^b$ is glycyl-amide, glycyl-Cys(S-paclitaxel)-amide, or (mini-PEG6)-Cys(S-paclitaxel)-amide,
provided at least one of $R^a$ or $R^b$ comprises 5-paclitaxel.

11. The high affinity CXCR4 selective binding ligand peptide conjugate of claim 1 of the Formula:

(SEQ ID NO: 2)

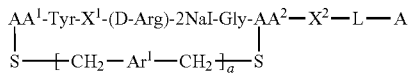
III or a pharmaceutically acceptable salt thereof, wherein:
a is 0 or 1;
AA$^1$ along with the sulfur atom that is attached thereto is 3-mercaptopropionic acid, optionally substituted cysteine, or optionally substituted homocysteine, wherein A is optionally attached to α-amino group of said cysteine or homocysteine;
AA$^2$ along with the sulfur atom that is attached thereto is cysteine or homocysteine;
Ar$^1$ is an optionally substituted aryl;

X$^1$ is Arg, Dap, Dab, Orn, Lys, Dap(iPr), Dab(iPr), Orn(iPr), or Lys(iPr);
X$^2$ is Arg, Dap, Dab, Orn, Lys, Dap(iPr), Dab(iPr), Orn(iPr), Lys(iPr), D-Arg, D-Dap, D-Dab, D-Orn, D-Lys, D-Dap(iPr), D-Dab(iPr), D-Orn(iPr), D-Lys (iPr), or absent;
L is an optional linker; and
A is as defined in claim 1.

12. The high affinity CXCR4 selective binding ligand peptide conjugate of claim 1, wherein A is selected from the group consisting of HIV protease inhibitors, HIV fusion inhibitors, HIV reverse transcriptase inhibitors, HIV integrase inhibitors, HIV entry inhibitors, and a combination thereof.

13. The high affinity CXCR4 selective binding ligand peptide conjugate of claim 12, wherein A is HIV fusion inhibitor enfuvirtide.

14. A composition comprising a high affinity CXCR4 selective binding ligand peptide conjugate of claim 1 and a pharmaceutically acceptable carrier, diluent, excipient or a combination thereof.

15. A diagnostic or an imaging kit comprising a high affinity CXCR4 selective binding ligand peptide conjugate (PC) of claim 1, wherein A of Formula I is a diagnostic agent or an imaging agent.

16. A method for imaging cancer cells in a patient comprising:
administering to a patient an imaging effective amount of a high affinity CXCR4 selective binding ligand peptide conjugate of claim 4; and
imaging cancer cells in said patient using an imaging apparatus.

17. A method for treating cancer in a patient, said method comprising administering a therapeutically effective amount of a compound of claim 11 to a cancer patient, wherein A is a cancer drug.

18. A method for treating a patient suffering from rheumatoid arthritis, pulmonary fibrosis, HIV infection, or a cancer, said method comprising administering a therapeutically effective amount of a compound of claim 11 to a patient in need of treatment thereof, wherein said cancer is selected from the group consisting of breast cancer, pancreatic cancer, melanoma, prostate cancer, kidney cancer, neuroblastoma, non-Hodgkin's lymphoma, lung cancer, ovarian cancer, colorectal cancer, multiple myeloma, glioblastoma multiforme, and chronic lymphocytic leukemia.

19. A high affinity CXCR4 selective binding ligand peptide conjugate (PC) of the Formula:

P-(-L-A)$_n$  I or a pharmaceutically acceptable salt thereof, wherein
n is an integer from 2 to about 5 or the sum of (the total number of side-chain functional groups within P)
A is a therapeutic agent;
L is a bifunctional linker or absent; and
P is a high affinity CXCR4 selective binding peptidyl ligand of the formula:

(SEQ ID NO: 1)

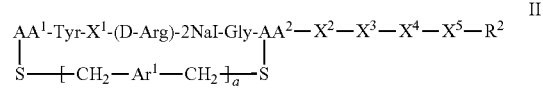
II wherein:
a is 0 or 1;
AA$^1$ along with the sulfur atom that is attached thereto is 3-mercaptopropionic acid, optionally substituted cysteine, or optionally substituted homocysteine;
AA$^2$ along with the sulfur atom that is attached thereto is cysteine or homocysteine;
Ar$^1$ is an optionally substituted aryl;
X$^1$ is Arg, Dap, Dab, Orn, Lys, Dap(iPr), Dab(iPr), Orn(iPr), or Lys(iPr);
X$^2$ is Arg, Dap, Dab, Orn, Lys, Dap(iPr), Dab(iPr), Orn(iPr), Lys(iPr), D-Arg, D-Dap, D-Dab, D-Orn, D-Lys, D-Dap(iPr), D-Dab(iPr), D-Orn(iPr), D-Lys(iPr), or absent;
X$^3$ is Lys, Gly or absent;
X$^4$ is Lys, Phe, 2Nal, 1Nal, the D-isomer thereof, Gly, or absent;
X$^5$ is Lys, Gly or absent; and
R$^2$ is —OR$^4$ or —NHR$^5$, wherein R$^4$ and R$^5$ are H, alkyl, optionally substituted aryl or optionally substituted aralkyl.

20. The high affinity CXCR4 selective binding ligand peptide conjugate of claim 19, wherein each of said therapeutic agent is independently selected from the group consisting of bleomycin, calicheamicin, daunorubicin, docetaxel, doxorubicin, irinotecan, mertansine, monomethyl auristatin E, paclitaxel, SN-38, tesirine, topotecan, tubulysin, vinca alkaloids, and an analog or derivative thereof, and a combination thereof.

* * * * *

SEQUENCE LISTING

```
<160> NUMBER OF SEQ ID NOS: 12

<210> SEQ ID NO 1
<211> LENGTH: 11
<212> TYPE: PRT
<213> ORGANISM: Artificial Sequence
<220> FEATURE:
<223> OTHER INFORMATION: Compound of Formula II
<220> FEATURE:
<221> NAME/KEY: MISC_FEATURE
<222> LOCATION: (1)..(1)
<223> OTHER INFORMATION: Along with the sulfur atom that is attached to
      is 3-mercaptopropionic acid (MPA), optionally N-substituted
      cysteine or optionally N-substituted homocysteine
<220> FEATURE:
<221> NAME/KEY: MISC_FEATURE
<222> LOCATION: (1)..(7)
<223> OTHER INFORMATION: Forms cyclic structure via sulfur atoms and a
      linker -(CH2-Ar1-CH2)-, where Ar1 is an optionally substituted
      aryl
<220> FEATURE:
<221> NAME/KEY: MISC_FEATURE
```

```
<222> LOCATION: (3)..(3)
<223> OTHER INFORMATION: can be Arg, Dap, Dab, Orn, Lys, Dap(iPr),
      Dab(iPr), Orn(iPr), or Lys(iPr)
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2Nal
<220> FEATURE:
<221> NAME/KEY: MISC_FEATURE
<222> LOCATION: (7)..(7)
<223> OTHER INFORMATION: Along with the sulfur atom that is attached to
      is cysteine or homocysteine
<220> FEATURE:
<221> NAME/KEY: MISC_FEATURE
<222> LOCATION: (8)..(8)
<223> OTHER INFORMATION: can be Arg, Dap, Dab, Orn, Lys, Dap(iPr),
      Dab(iPr), Orn(iPr), Lys(iPr), D-Arg, D-Dap, D-Dab, D-Orn, D-Lys,
      D-Dap(iPr), D-Dab(iPr), D-Orn(iPr), D-Lys(iPr), or absent
<220> FEATURE:
<221> NAME/KEY: MISC_FEATURE
<222> LOCATION: (9)..(9)
<223> OTHER INFORMATION: can be Gly or absent
<220> FEATURE:
<221> NAME/KEY: MISC_FEATURE
<222> LOCATION: (10)..(10)
<223> OTHER INFORMATION: can be Lys, Phe, 2Nal, 1Nal, the D-isomer
      thereof, Gly, or absent
<220> FEATURE:
<221> NAME/KEY: MISC_FEATURE
<222> LOCATION: (11)..(11)
<223> OTHER INFORMATION: Lys, Gly or absent
<220> FEATURE:
<221> NAME/KEY: MISC_FEATURE
<222> LOCATION: (11)..(11)
<223> OTHER INFORMATION: terminal -OH group is replaced with -OR4 or
      -NHR5, wherein R4 and R5 is H, alkyl, optionally substituted aryl,
      or optionally substituted aralkyl

<400> SEQUENCE: 1

Xaa Tyr Xaa Arg Xaa Gly Xaa Xaa Xaa Xaa Xaa
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Compound of Formula III
<220> FEATURE:
<221> NAME/KEY: MISC_FEATURE
<222> LOCATION: (1)..(1)
<223> OTHER INFORMATION: along with the sulfur atom that is attached
      thereto is 3-mercaptopropionic acid, optionally substituted
      cysteine, or optionally substituted homocysteine
<220> FEATURE:
<221> NAME/KEY: MISC_FEATURE
<222> LOCATION: (1)..(7)
<223> OTHER INFORMATION: Forms cyclic structure via sulfur atoms and a
      linker -(CH2-Ar1-CH2)-, where Ar1 is an optionally substituted
      aryl
<220> FEATURE:
<221> NAME/KEY: MISC_FEATURE
<222> LOCATION: (3)..(3)
<223> OTHER INFORMATION: can be Arg, Dap, Dab, Orn, Lys, Dap(iPr),
      Dab(iPr), Orn(iPr), or Lys(iPr)
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2Nal
```

```
<220> FEATURE:
<221> NAME/KEY: MISC_FEATURE
<222> LOCATION: (7)..(7)
<223> OTHER INFORMATION: along with the sulfur atom that is attached
      thereto is cysteine or homocysteine
<220> FEATURE:
<221> NAME/KEY: MISC_FEATURE
<222> LOCATION: (7)..(7)
<223> OTHER INFORMATION: along with the sulfur atom that is attached
      thereto is cysteine or homocysteine
<220> FEATURE:
<221> NAME/KEY: MISC_FEATURE
<222> LOCATION: (8)..(8)
<223> OTHER INFORMATION: can be Arg, Dap, Dab, Orn, Lys, Dap(iPr),
      Dab(iPr), Orn(iPr), Lys(iPr), D-Arg, D-Dap, D-Dab, D-Orn, D-Lys,
      D-Dap(iPr), D-Dab(iPr), D-Orn(iPr), D-Lys(iPr), or absent

<400> SEQUENCE: 2

Xaa Tyr Xaa Arg Xaa Gly Xaa Xaa
1               5

<210> SEQ ID NO 3
<211> LENGTH: 8
<212> TYPE: PRT
<213> ORGANISM: Artificial Sequence
<220> FEATURE:
<223> OTHER INFORMATION: S-Paclitaxel
<220> FEATURE:
<221> NAME/KEY: MISC_FEATURE
<222> LOCATION: (1)..(7)
<223> OTHER INFORMATION: cyclic structure is formed between the alpha-
      amino of phenylalanince
<220> FEATURE:
<221> NAME/KEY: MISC_FEATURE
<222> LOCATION: (3)..(3)
<223> OTHER INFORMATION: side-chain amino acid of lysine is substituted
      with iso-propyl group
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: D-isomer
<220> FEATURE:
<221> NAME/KEY: MISC_FEATURE
<222> LOCATION: (8)..(8)
<223> OTHER INFORMATION: side-chain amino group is substituted with iso-
      propyl.

<400> SEQUENCE: 3

Phe Tyr Lys Arg Xaa Gly Gln Lys
1               5

<210> SEQ ID NO 4
<211> LENGTH: 8
<212> TYPE: PRT
<213> ORGANISM: Artificial Sequence
<220> FEATURE:
<223> OTHER INFORMATION: linked to paclitaxel
<220> FEATURE:
<221> NAME/KEY: MISC_FEATURE
<222> LOCATION: (1)..(7)
<223> OTHER INFORMATION: cyclic structure is formed by formation of a
      di-sulfide linkage between sulfur atoms of two cysteine groups.
<220> FEATURE:
<221> NAME/KEY: MISC_FEATURE
<222> LOCATION: (3)..(3)
<223> OTHER INFORMATION: side-chain amino group is substituted with
      isopropyl
```

```
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: NaI
<220> FEATURE:
<221> NAME/KEY: MISC_FEATURE
<222> LOCATION: (8)..(8)
<223> OTHER INFORMATION: side-chain amino group is substituted with
      isopropyl

<400> SEQUENCE: 4

Cys Tyr Lys Arg Xaa Gly Cys Lys
1               5

<210> SEQ ID NO 5
<211> LENGTH: 8
<212> TYPE: PRT
<213> ORGANISM: Artificial Sequence
<220> FEATURE:
<223> OTHER INFORMATION: linked to paclitaxel
<220> FEATURE:
<221> NAME/KEY: MISC_FEATURE
<222> LOCATION: (1)..(1)
<223> OTHER INFORMATION: homocysteine
<220> FEATURE:
<221> NAME/KEY: MISC_FEATURE
<222> LOCATION: (1)..(7)
<223> OTHER INFORMATION: cyclic structure is formed by formation of a
      di-sulfide linkage between sulfur atoms of homocysteine and
      cysteine
<220> FEATURE:
<221> NAME/KEY: MISC_FEATURE
<222> LOCATION: (3)..(3)
<223> OTHER INFORMATION: side-chain amino group is substituted with
      isopropyl
<220> FEATURE:
<221> NAME/KEY: MISC_FEATURE
<222> LOCATION: (4)..(4)
<223> OTHER INFORMATION: D-isome
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (8)..(8)
<223> OTHER INFORMATION: side-chain amino group is substituted with
      isopropyl

<400> SEQUENCE: 5

Xaa Tyr Lys Arg Xaa Gly Cys Lys
1               5

<210> SEQ ID NO 6
<211> LENGTH: 8
<212> TYPE: PRT
<213> ORGANISM: Artificial Sequence
<220> FEATURE:
<223> OTHER INFORMATION: linked to paclitaxel
<220> FEATURE:
<221> NAME/KEY: MISC_FEATURE
<222> LOCATION: (1)..(7)
<223> OTHER INFORMATION: cyclic structure is formed by formation of a
      di-sulfide linkage between sulfur atoms of cysteine and
      homocysteine
<220> FEATURE:
<221> NAME/KEY: MISC_FEATURE
<222> LOCATION: (3)..(3)
<223> OTHER INFORMATION: side-chain amino group is substituted with
      isopropyl
<220> FEATURE:
```

```
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: homocysteine
<220> FEATURE:
<221> NAME/KEY: MISC_FEATURE
<222> LOCATION: (8)..(8)
<223> OTHER INFORMATION: side-chain amino group is substituted with
      isopropyl

<400> SEQUENCE: 6

Cys Tyr Lys Arg Xaa Gly Xaa Lys
1               5

<210> SEQ ID NO 7
<211> LENGTH: 8
<212> TYPE: PRT
<213> ORGANISM: Artificial Sequence
<220> FEATURE:
<223> OTHER INFORMATION: linked to paclitaxel
<220> FEATURE:
<221> NAME/KEY: MISC_FEATURE
<222> LOCATION: (1)..(7)
<223> OTHER INFORMATION: Forms cyclic structure via sulfur atoms and a
      linker -(CH2-(1,2-Ph)-CH2)-.
<220> FEATURE:
<221> NAME/KEY: MISC_FEATURE
<222> LOCATION: (3)..(3)
<223> OTHER INFORMATION: side-chain amino group is substituted with
      isopropyl
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (8)..(8)
<223> OTHER INFORMATION: side-chain amino group is substituted with
      isopropyl

<400> SEQUENCE: 7

Cys Tyr Lys Arg Xaa Gly Cys Leu
1               5

<210> SEQ ID NO 8
<211> LENGTH: 7
<212> TYPE: PRT
<213> ORGANISM: Artificial Sequence
<220> FEATURE:
<223> OTHER INFORMATION: Example 1 statring material
<220> FEATURE:
<221> NAME/KEY: MISC_FEATURE
<222> LOCATION: (1)..(1)
<223> OTHER INFORMATION: protected with Mmt
<220> FEATURE:
<221> NAME/KEY: MISC_FEATURE
<222> LOCATION: (2)..(2)
<223> OTHER INFORMATION: protected with tBu
<220> FEATURE:
<221> NAME/KEY: MISC_FEATURE
<222> LOCATION: (3)..(3)
<223> OTHER INFORMATION: side-chain amino group is substituted with
      isopropyl
<220> FEATURE:
```

```
<221> NAME/KEY: MISC_FEATURE
<222> LOCATION: (3)..(3)
<223> OTHER INFORMATION: protected with Boc
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (4)..(4)
<223> OTHER INFORMATION: protected with Pbf
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (6)..(6)
<223> OTHER INFORMATION: side-chain amino group is substituted with
      isopropyl
<220> FEATURE:
<221> NAME/KEY: MISC_FEATURE
<222> LOCATION: (6)..(6)
<223> OTHER INFORMATION: protected with Boc
<220> FEATURE:
<221> NAME/KEY: MISC_FEATURE
<222> LOCATION: (6)..(6)
<223> OTHER INFORMATION: linked to -(mini-PEG6)-Cys(Trt)

<400> SEQUENCE: 8

Cys Tyr Lys Arg Xaa Cys Lys
1               5

<210> SEQ ID NO 9
<211> LENGTH: 10
<212> TYPE: PRT
<213> ORGANISM: Artificial Sequence
<220> FEATURE:
<223> OTHER INFORMATION: Reagent of Example 2
<220> FEATURE:
<221> NAME/KEY: MISC_FEATURE
<222> LOCATION: (1)..(1)
<223> OTHER INFORMATION: protected with Trt
<220> FEATURE:
<221> NAME/KEY: MISC_FEATURE
<222> LOCATION: (2)..(2)
<223> OTHER INFORMATION: protected with Mmt
<220> FEATURE:
<221> NAME/KEY: MISC_FEATURE
<222> LOCATION: (3)..(3)
<223> OTHER INFORMATION: protected with tBu
<220> FEATURE:
<221> NAME/KEY: MISC_FEATURE
<222> LOCATION: (4)..(4)
<223> OTHER INFORMATION: side-chain amino group is substituted with
      isopropyl
<220> FEATURE:
<221> NAME/KEY: MISC_FEATURE
<222> LOCATION: (4)..(4)
<223> OTHER INFORMATION: protected with Boc
<220> FEATURE:
<221> NAME/KEY: MISC_FEATURE
<222> LOCATION: (5)..(5)
<223> OTHER INFORMATION: D-isomer
<220> FEATURE:
<221> NAME/KEY: MISC_FEATURE
<222> LOCATION: (5)..(5)
<223> OTHER INFORMATION: protected with Pbf
<220> FEATURE:
<221> NAME/KEY: MISC_FEATURE
<222> LOCATION: (6)..(6)
<223> OTHER INFORMATION: 2NaI
<220> FEATURE:
<221> NAME/KEY: MISC_FEATURE
<222> LOCATION: (8)..(8)
<223> OTHER INFORMATION: protected with Mmt
<220> FEATURE:
```

```
<221> NAME/KEY: MISC_FEATURE
<222> LOCATION: (9)..(9)
<223> OTHER INFORMATION: side-chain amino group is substituted with
      isopropyl
<220> FEATURE:
<221> NAME/KEY: MISC_FEATURE
<222> LOCATION: (9)..(9)
<223> OTHER INFORMATION: protected with Boc

<400> SEQUENCE: 9

Cys Cys Tyr Lys Arg Xaa Gly Cys Lys Gly
1               5                   10

<210> SEQ ID NO 10
<211> LENGTH: 10
<212> TYPE: PRT
<213> ORGANISM: Artificial Sequence
<220> FEATURE:
<223> OTHER INFORMATION: reagent for example 4
<220> FEATURE:
<221> NAME/KEY: MISC_FEATURE
<222> LOCATION: (1)..(1)
<223> OTHER INFORMATION: protected with Trt
<220> FEATURE:
<221> NAME/KEY: MISC_FEATURE
<222> LOCATION: (1)..(2)
<223> OTHER INFORMATION: linker (mini-PEG6) is present between two
      cysteine groups
<220> FEATURE:
<221> NAME/KEY: MISC_FEATURE
<222> LOCATION: (2)..(2)
<223> OTHER INFORMATION: protected wtih Mmt
<220> FEATURE:
<221> NAME/KEY: MISC_FEATURE
<222> LOCATION: (3)..(3)
<223> OTHER INFORMATION: protected wtih tBu
<220> FEATURE:
<221> NAME/KEY: MISC_FEATURE
<222> LOCATION: (4)..(4)
<223> OTHER INFORMATION: side-chain amino group is substituted with
      isopropyl
<220> FEATURE:
<221> NAME/KEY: MISC_FEATURE
<222> LOCATION: (4)..(4)
<223> OTHER INFORMATION: protected with Boc
<220> FEATURE:
<221> NAME/KEY: MISC_FEATURE
<222> LOCATION: (5)..(5)
<223> OTHER INFORMATION: D-isomer
<220> FEATURE:
<221> NAME/KEY: MISC_FEATURE
<222> LOCATION: (5)..(5)
<223> OTHER INFORMATION: protected with Pbf
<220> FEATURE:
<221> NAME/KEY: MISC_FEATURE
<222> LOCATION: (6)..(6)
<223> OTHER INFORMATION: 2NaI
<220> FEATURE:
<221> NAME/KEY: MISC_FEATURE
<222> LOCATION: (8)..(8)
<223> OTHER INFORMATION: protected with Mmt
<220> FEATURE:
<221> NAME/KEY: MISC_FEATURE
<222> LOCATION: (9)..(9)
<223> OTHER INFORMATION: side-chain amino group is substituted with
      isopropyl
<220> FEATURE:
<221> NAME/KEY: MISC_FEATURE
<222> LOCATION: (9)..(9)
<223> OTHER INFORMATION: protected with Boc

<400> SEQUENCE: 10

Cys Cys Tyr Leu Arg Xaa Gly Cys Leu Gly
1               5                   10
```

-continued

```
<210> SEQ ID NO 11
<211> LENGTH: 10
<212> TYPE: PRT
<213> ORGANISM: Artificial Sequence
<220> FEATURE:
<223> OTHER INFORMATION: reagent for example 5
<220> FEATURE:
<221> NAME/KEY: MISC_FEATURE
<222> LOCATION: (2)..(2)
<223> OTHER INFORMATION: protected with tBu
<220> FEATURE:
<221> NAME/KEY: MISC_FEATURE
<222> LOCATION: (3)..(3)
<223> OTHER INFORMATION: side-chain amino group is substituted with
      isopropyl
<220> FEATURE:
<221> NAME/KEY: MISC_FEATURE
<222> LOCATION: (3)..(3)
<223> OTHER INFORMATION: protected with Boc
<220> FEATURE:
<221> NAME/KEY: MISC_FEATURE
<222> LOCATION: (4)..(4)
<223> OTHER INFORMATION: protected with Pbf
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: protected with OAll
<220> FEATURE:
<221> NAME/KEY: MISC_FEATURE
<222> LOCATION: (7)..(7)
<223> OTHER INFORMATION: D-isomer
<220> FEATURE:
<221> NAME/KEY: MISC_FEATURE
<222> LOCATION: (8)..(8)
<223> OTHER INFORMATION: side-chain amino group is substituted with
      isopropyl
<220> FEATURE:
<221> NAME/KEY: MISC_FEATURE
<222> LOCATION: (8)..(8)
<223> OTHER INFORMATION: protected with Boc
<220> FEATURE:
<221> NAME/KEY: MISC_FEATURE
<222> LOCATION: (8)..(9)
<223> OTHER INFORMATION: linker (mini-PEG6) is present between lysine
      and cysteine
<220> FEATURE:
<221> NAME/KEY: MISC_FEATURE
<222> LOCATION: (9)..(9)
<223> OTHER INFORMATION: protected with Trt

<400> SEQUENCE: 11

Phe Tyr Lys Arg Xaa Gly Gln Lys Cys Gly
1               5                   10

<210> SEQ ID NO 12
<211> LENGTH: 10
<212> TYPE: PRT
<213> ORGANISM: Artificial Sequence
<220> FEATURE:
<223> OTHER INFORMATION: reagent for Example 6
<220> FEATURE:
<221> NAME/KEY: MISC_FEATURE
<222> LOCATION: (1)..(1)
<223> OTHER INFORMATION: protected with Mmt
<220> FEATURE:
<221> NAME/KEY: MISC_FEATURE
<222> LOCATION: (2)..(2)
<223> OTHER INFORMATION: protected with tBu
<220> FEATURE:
```

```
<221> NAME/KEY: MISC_FEATURE
<222> LOCATION: (3)..(3)
<223> OTHER INFORMATION: side-chain amino group is substituted with
      isopropyl
<220> FEATURE:
<221> NAME/KEY: MISC_FEATURE
<222> LOCATION: (3)..(3)
<223> OTHER INFORMATION: protected with Boc
<220> FEATURE:
<221> NAME/KEY: MISC_FEATURE
<222> LOCATION: (4)..(4)
<223> OTHER INFORMATION: protected with Pbf
<220> FEATURE:
<221> NAME/KEY: MISC_FEATURE
<222> LOCATION: (4)..(4)
<223> OTHER INFORMATION: D-isomer
<220> FEATURE:
<221> NAME/KEY: MISC_FEATURE
<222> LOCATION: (5)..(5)
<223> OTHER INFORMATION: 2NaI
<220> FEATURE:
<221> NAME/KEY: MISC_FEATURE
<222> LOCATION: (7)..(7)
<223> OTHER INFORMATION: protected with Mmt
<220> FEATURE:
<221> NAME/KEY: MISC_FEATURE
<222> LOCATION: (8)..(8)
<223> OTHER INFORMATION: protected with Boc
<220> FEATURE:
<221> NAME/KEY: MISC_FEATURE
<222> LOCATION: (8)..(8)
<223> OTHER INFORMATION: side-chain amino group is substituted with
      isopropyl
<220> FEATURE:
<221> NAME/KEY: MISC_FEATURE
<222> LOCATION: (10)..(10)
<223> OTHER INFORMATION: protected with Trt

<400> SEQUENCE: 12

Cys Tyr Lys Arg Xaa Gly Cys Lys Gly Cys
1               5                   10
```